(12) United States Patent
Tekumalla et al.

(10) Patent No.: US 10,468,136 B2
(45) Date of Patent: Nov. 5, 2019

(54) METHOD AND SYSTEM FOR DATA PROCESSING TO PREDICT HEALTH CONDITION OF A HUMAN SUBJECT

(71) Applicant: Conduent Business Services, LLC, Dallas, TX (US)

(72) Inventors: Lavanya Sita Tekumalla, Bangalore (IN); Vaibhav Rajan, Bangalore (IN)

(73) Assignee: CONDUENT BUSINESS SERVICES, LLC, Florham Park, NJ (US)

( * ) Notice: Subject to any disclaimer, the term of this patent is extended or adjusted under 35 U.S.C. 154(b) by 279 days.

(21) Appl. No.: 15/249,648

(22) Filed: Aug. 29, 2016

(65) Prior Publication Data

US 2018/0060509 A1 Mar. 1, 2018

(51) Int. Cl.
*G16H 50/20* (2018.01)
*G06N 7/00* (2006.01)
*G06N 20/00* (2019.01)
*G06F 16/28* (2019.01)
*G16H 50/70* (2018.01)
(Continued)

(52) U.S. Cl.
CPC ........... *G16H 50/20* (2018.01); *G06F 16/285* (2019.01); *G06N 7/005* (2013.01); *G06N 20/00* (2019.01); *G16H 50/70* (2018.01); *G06N 5/003* (2013.01); *G06N 20/10* (2019.01); *G16H 10/60* (2018.01)

(58) Field of Classification Search
CPC .... G06F 19/3431; G06F 19/00; G06F 16/285; G16H 50/30; A61B 5/7267; G09B 23/281; G09B 23/32; G09B 23/34; G09B 17/00; G09B 17/003; G09B 17/04; G09B 19/04; G09B 19/06; G09B 7/02
See application file for complete search history.

(56) References Cited

U.S. PATENT DOCUMENTS 4,783,803 A * 11/1988 Baker ................... G10L 15/00
704/252
2001/0051765 A1* 12/2001 Walker .................. A61B 5/1112
600/300
(Continued)

OTHER PUBLICATIONS

Francis R Bach and Michael I Jordan. A probabilistic interpretation of canonical correlation analysis. 2005.
(Continued)

*Primary Examiner* — Neal Sereboff
(74) *Attorney, Agent, or Firm* — Jones Robb, PLLC

(57) ABSTRACT

Disclosed are embodiments of method and system to predict health condition of a human subject. The method comprises receiving historical human-subject related data including records corresponding to multiple data views. The method estimates one or more latent variables based on: a first value indicative of count of records in a cluster, a second value indicative of count of records, and a third value indicative of a parameter utilizable to predict a fourth value. The fourth value corresponds to selection probability of a D-vine pair copula family, of a D-vine mixture model, utilizable to model a cluster. The method generates the D-vine mixture model based on the estimated one or more latent variables. The method further comprises receiving multi-view data of a second human subject and predicting health condition of the second human subject based on the multi-view data using a classifier trained based on the estimated latent variables.

21 Claims, 4 Drawing Sheets

(51) Int. Cl.
*G16H 10/60* (2018.01)
*G06N 5/00* (2006.01)
*G06N 20/10* (2019.01)

(56) References Cited

U.S. PATENT DOCUMENTS

| | | | | |
|---|---|---|---|---|
| 2005/0278140 | A1* | 12/2005 | Wang | G01R 31/2894 |
| | | | | 702/179 |
| 2010/0134353 | A1* | 6/2010 | van Diggelen | G01S 19/05 |
| | | | | 342/357.66 |
| 2011/0119212 | A1* | 5/2011 | De Bruin | A61B 5/00 |
| | | | | 706/12 |
| 2012/0095300 | A1* | 4/2012 | McNair | A61B 5/021 |
| | | | | 600/300 |
| 2012/0143017 | A1* | 6/2012 | Snyder | G06N 99/005 |
| | | | | 600/300 |
| 2012/0223889 | A1* | 9/2012 | Medlock | G06F 3/04883 |
| | | | | 345/168 |
| 2012/0288881 | A1* | 11/2012 | Liu | G01N 33/6893 |
| | | | | 435/7.92 |
| 2012/0290599 | A1* | 11/2012 | Tian | G06F 17/30616 |
| | | | | 707/758 |
| 2015/0227691 | A1* | 8/2015 | Bhattacharya | G06F 19/322 |
| | | | | 705/3 |
| 2016/0133150 | A1* | 5/2016 | Sutz | G09B 17/003 |
| | | | | 434/178 |
| 2016/0246931 | A1* | 8/2016 | Rajan | G06F 19/345 |
| 2017/0025043 | A1* | 1/2017 | Chenoweth | G09B 23/281 |

OTHER PUBLICATIONS

Pavel Berkhin. A survey of clustering data mining techniques. In Grouping multidimensional data, pp. 25-71. Springer, 2006.
Mike West Michael Escobar. Bayesian density estimation and inference using mixtures. In Journal of American Statistical Association, 1995.
Xiaoli Zhang Fern, Carla E Brodley, and Mark A Friedl. Correlation clustering for learning mixtures of canonical correlation models. In SDM, pp. 439-448. SIAM, 2005.
Ryohei Fujimaki, Yasuhiro Sogawa, and Satoshi Morinaga. Online heterogeneous mixture modeling with marginal and copula selection. In Proceedings of the 17th ACM SIGKDD International Conference on Knowledge Discovery and Data mining, pp. 645-653, 2011.
David Hardoon, Sandor Szedmak, and John Shawe-Taylor. Canonical correlation analysis: An overview with application to learning methods. Neural computation, 16(12):2639-2664, 2004.
Peter D. Hoff. Extending the rank likelihood for semiparametric copula estimation. The Annals of Applied Statistics, 1(1):265-283, 2007.
Harold Hotelling. Relations between two sets of variates. Biometrika, pp. 321-377, 1936.
Claudia Plant and Christian Böhm. INCONCO: interpretable clustering of numerical and categorical objects. In Proceedings of the 17th ACM SIGKDD international conference on Knowledge discovery and data mining, pp. 1127-1135. ACM, 2011.
Anil K Jain. Data clustering: 50 years beyond kmeans. Pattern Recognition Letters, 31(8):651-666, 2010.
Samuel Kaski, Janne Nikkila, Janne Sinkkonen, Leo Lahti, Juha EA Knuuttila, and Christophe Roos. Associative clustering for exploring dependencies between functional genomics data sets. IEEE/ACM Transactions on Computational Biology and Bioinformatics(TCBB), 2(3):203-216, 2005.
Francis R Bach and Michael I Jordan. Kernel independent component analysis. The Journal of Machine Learning Research, 3:1-48, 2003.
Arto Klami and Samuel Kaski. Non-parametric dependent components. In ICASSP (5), pp. 209-212, 2005.
Marina Meila. Comparing clusterings: an information based distance. Journal of Multivariate Analysis, 98(5):873-895, 2007.
Daeyoung Kim, Jong-Min Kim, Shu-Min Liao, and Yoon-Sung Jung. Mixture of d-vine copulas for modeling dependence. Computational Statistics & Data Analysis, 64:1-19, 2013.
Radford M. Neal. Markov chain sampling methods for dirichlet process mixture models. In Journal of Computational and Graphical Stats. USENIX, 2000.
Claudia Plant. Dependency clustering across measurement scales. In Proceedings of the 18th ACM SIGKDD international conference on Knowledge discovery and data mining, pp. 361-369. ACM, 2012.
Arto Klami and Samuel Kaski. Probabilistic approach to detecting dependencies between data sets. Neurocomputing, 72(1):39-46, 2008.
M. Rey and V. Roth. Copula mixture model for dependency-seeking clustering. In International Conference on Machine Learning, 2012.
Michael S Smith and Mohamad A Khaled. Estimation of copula models with discrete margins via Bayesian data augmentation. Journal of the American Statistical Association, 107(497):290-303, 2012.
Y. W. Teh. Dirichlet processes. In Encyclopedia of Machine Learning. Springer, 2010.
Nguyen Xuan Vinh, Julien Epps, and James Bailey. Information theoretic measures for clusterings comparison: Variants, properties, normalization and correction for chance. The Journal of Machine Learning Research, 11:2837-2854, 2010.

* cited by examiner

METHOD AND SYSTEM FOR DATA PROCESSING TO PREDICT HEALTH CONDITION OF A HUMAN SUBJECT

TECHNICAL FIELD

The presently disclosed embodiments are related, in general, to data processing in healthcare. More particularly, the presently disclosed embodiments are related to methods and systems for predicting the health condition of a human subject.

BACKGROUND

Modern-day organizations entail real-time data measurements, critical for operational requirements, from multiple data sources. Such data sources may be intrinsic or extrinsic to the organizations. Examples of intrinsic data sources may include customer relationship management (CRM) software, supply chain management (SCM) software, human resource management (HRM) software, and/or other such enterprise resource management (ERP) software modules. Examples of extrinsic data sources may include external data sources, websites, database servers, and the like. For example, the CRM software may generate data that may be required to draw useful insights therefrom to support decision-making and provide a competitive edge to the organization.

One significant use case of such multi-source data, also called data views, may be that of the healthcare industry, which maintains various types of records of human subjects collected from disparate data sources. Examples of such data views may include medical diagnosis information, medical insurance information, hospital data, demographic data, and/or other medical history data associated with the human subject. The multi-source data (or multi-view data) associated with the healthcare industry may be analyzed using various statistical techniques to identify trends and categories within the dataset based on a certain criteria (such as a medical or insurance default risk profile of a human subject).

However, there may be several inherent challenges in the analysis of the data views. For instance, the multi-view data may be of mixed data types, such as categorical and numerical data types. Further, the number of dimensions, such as number of data fields, associated with each data view may be significant and/or different with respect to each other. In addition, to generate meaningful insights, it may be challenging to simultaneously model dependencies both within each data view and between different data views across the different data sources. Thus, a technique is required to efficiently process such multi-view data in real time to overcome the aforesaid challenges.

Further limitations and disadvantages of conventional and traditional approaches will become apparent to one skilled in the art through comparison of described system with some aspects of the present disclosure, as set forth in the remainder of the present application and with reference to the drawings.

SUMMARY

According to embodiments illustrated herein there is provided a method for data processing to predict health condition of a human subject. The method may comprise reception of historical data that may comprise one or more records of one or more first human subjects from a database over a communication network by one or more transceivers in a first computing device. Each of the one or more records in the historical data may include data corresponding to a plurality of data views. Thereafter, for each of the plurality of data views, the method may include clustering of data corresponding to the data view in the historical data into one or more clusters by one or more processors in the first computing. Each of the one or more clusters may be modeled using a D-vine pair copula family from one or more D-vine pair copula families associated with a D-vine mixture model, by sampling a plurality of latent variables based on a rank transformation of the historical data.

For each of the plurality of data views, the method may further include estimation of one or more of the plurality of latent variables based on a first value, a second value, and a third value by the one or more processors. The first value may be indicative of a count of the one or more records clustered in a cluster from the one or more clusters corresponding to the data view, while the second value may be indicative of a count of the one or more records. Further, the third value may be indicative of a parameter utilizable to predict a fourth value. The fourth value may correspond to a probability of selecting the D-vine pair copula family from the one or more D-vine pair copula families to model the cluster from the one or more clusters corresponding to the data view. The method may further include generation of the D-vine mixture model that may include the selected D-vine pair copula family for each of the plurality of data views, based on the estimated one or more of the plurality of latent variables, by the one or more processors. After the generation of the D-vine mixture model, the method may further include training of a classifier based on the generated D-vine mixture model by the one or more processors. Thereafter, the method may include reception of multi-view data associated with a second human subject from one or more data sources and/or one or more second computing devices over the communication network by the one or more transceivers. Further, the method may include prediction of health condition of the second human subject by utilizing the trained classifier based on the received multi-view data associated with the second human subject, by the one or more processors. Thereafter, the method may include transmission of the predicted health condition of the second human subject to the one or more second computing devices over the communication network by the one or more transceivers. The predicted health condition of the second human subject may be displayed at the one or more second computing devices.

According to embodiment illustrated herein there is provided a system for data processing to predict health condition of a human subject. The system may comprise one or more transceivers and one or more processors in an application server. The one or more transceivers may be configured to receive historical data that may comprise one or more records of one or more first human subjects from a database over a communication network. Each of the one or more records may include data corresponding to a plurality of data views. For each of the plurality of data views, the one or more processors may be configured to cluster data corresponding to the data view in the historical data into one or more clusters. Each of the one or more clusters may be modeled using a D-vine pair copula family from one or more D-vine pair copula families associated with a D-vine mixture model, by sampling a plurality of latent variables based on a rank transformation of the historical data.

For each of the plurality of data views, the one or more processors may be further configured to estimate one or more of the plurality latent variable based on a first value, a second value, and a third value. The first value may be indicative of a count of the one or more records clustered in a cluster from the one or more clusters corresponding to the data view, while the second value may be indicative of a count of the one or more records. Further, the third value may be indicative of a parameter utilizable to predict a fourth value. The fourth value may correspond to a probability of selecting the D-vine pair copula family from the one or more D-vine pair copula families to model the cluster from the one or more clusters corresponding to the data view. The one or more processors may be further configured to generate the D-vine mixture model that may include the selected D-vine pair copula family for each of the plurality of data views, based on the estimated one or more of the plurality of latent variables. The one or more processors may be further configured to train a classifier based on the generated D-vine mixture model. In addition, the one or more transceivers may be further configured to receive multi-view data associated with a second human subject from one or more data sources and/or one or more second computing devices over the communication network. Thereafter, the one or more processors may be further configured to predict health condition of the second human subject by utilizing the trained classifier based on the received multi-view data associated with the second human subject.

According to embodiments illustrated herein, there is provided a computer program product for use with a first computing device. The computer program product comprises a non-transitory computer readable medium storing a computer program code for data processing to predict health condition of a human subject. The computer program code is executable by one or more processors in the first computing device to receive historical data that may comprise one or more records of one or more first human subjects. The historical data may be received by one or more transceivers in the first computing device, from a database over a communication network. Each of the one or more records may include data corresponding to a plurality of data views. For each of the plurality of data views, the computer program code is further executable by the one or more processors to cluster data corresponding to the data view in the historical data into one or more clusters. Each of the one or more clusters may be modeled using a D-vine pair copula family from one or more D-vine pair copula families associated with a D-vine mixture model, by sampling a plurality of latent variables based on a rank transformation of the historical data.

For each of the plurality of data views, the computer program code is further executable by the one or more processors to estimate one or more of the plurality of latent variables based on a first value, a second value, and a third value. The first value may be indicative of a count of the one or more records clustered in a cluster from the one or more clusters corresponding to the data view, while the second value may be indicative of a count of the one or more records. Further, the third value may be indicative of a parameter utilizable to predict a fourth value. The fourth value may correspond to a probability of selecting the D-vine pair copula family from the one or more D-vine pair copula families to model the cluster from the one or more clusters corresponding to the data view. The computer program code is further executable by the one or more processors to generate the D-vine mixture model that may include the selected D-vine pair copula family for each of the plurality of data views, based on the estimated one or more of the plurality of latent variables. The computer program code is further executable by the one or more processors to train a classifier based on the generated D-vine mixture model. In addition, the multi-view data associated with a second human subject is received from one or more data sources and/or one or more second computing devices over the communication network. Thereafter, the computer program code is further executable by the one or more processors to predict health condition of the second human subject by utilizing the trained classifier based on the received multi-view data associated with the second human subject.

BRIEF DESCRIPTION OF DRAWINGS

The accompanying drawings illustrate various embodiments of system, method, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not limit, the scope in any manner, wherein similar designations denote similar elements, and in which.

DETAILED DESCRIPTION

Figure 1:
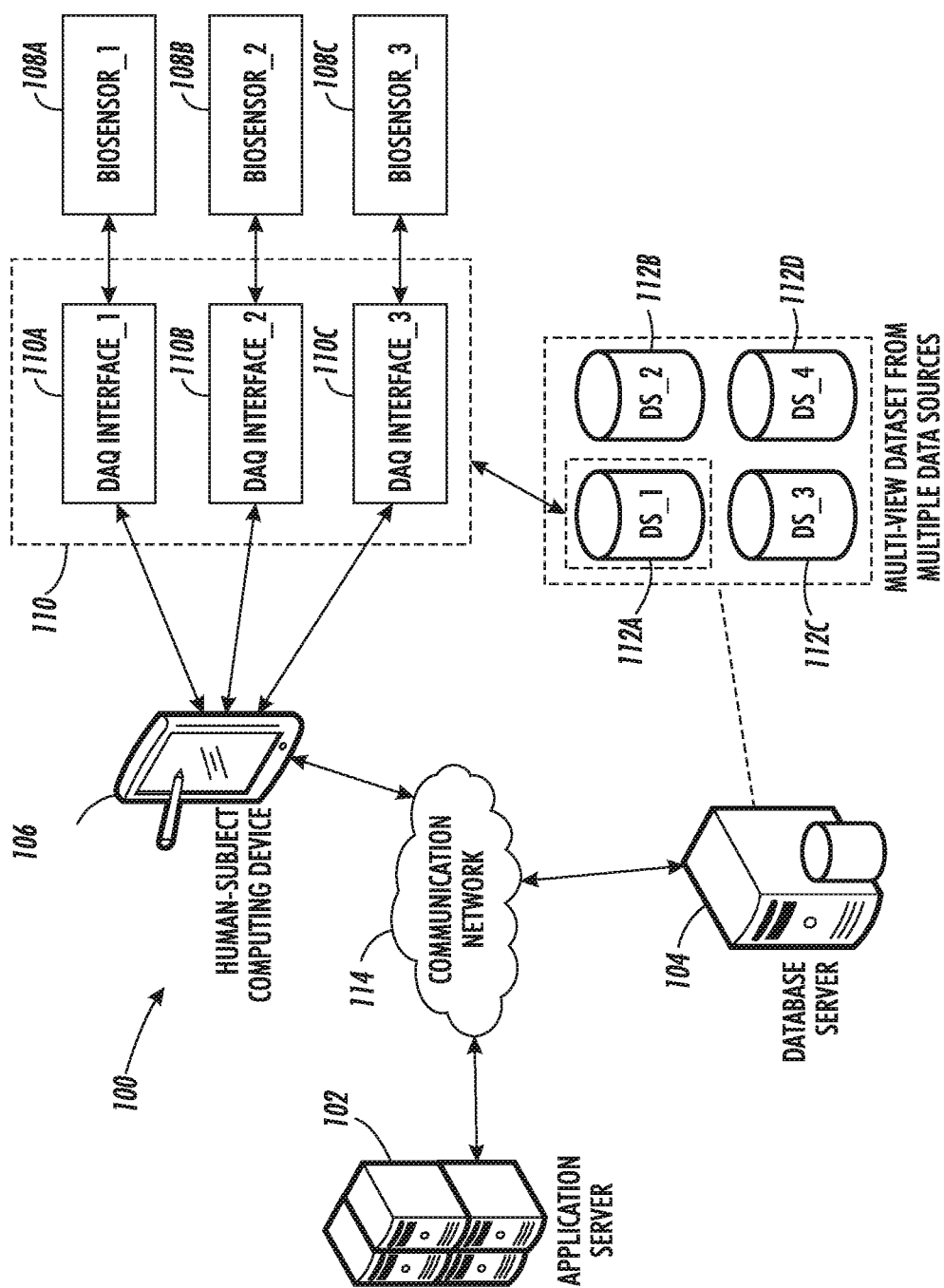
FIG. 1 is a block diagram of a system environment, in which various embodiments can be implemented, in accordance with at least one embodiment.

The present disclosure is best understood with reference to the detailed figures and descriptions set forth herein. Various embodiments are discussed below with reference to the figures. However, those skilled in the art will readily appreciate that the detailed descriptions given herein with respect to the figures are simply for explanatory purposes, as the method and system may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "at least one embodiment," "an embodiment," "one example," "an example," "for example" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

Definitions: The following terms shall have, for the purposes of this application, the respective meanings set forth below.

A "multivariate dataset" refers to a dataset that includes specific observations (such as "n" observations) of an m-dimensional variable. For example, medical record data may include measurements of one or more physiological parameters of one or more patients, where the one or more physiological parameters correspond to the m-dimensions and the one or more patients correspond to "n" observations. Such medical record data is an example of the multivariate dataset.

"Historical data" refers to a dataset that may be generated over a historic period of time. The historical data may include records associated with one or more subjects or events. Each record may include one or more fields, each of which may correspond to an individual observation related to a measured parameter. Each record may also include other fields apart from the measure of physiological parameters, as mentioned below.

A "healthcare dataset" refers to a multivariate dataset that includes data obtained from the healthcare industry. In an embodiment, the healthcare dataset may correspond to a patient record data, hospital data, medical insurance data, diagnostics data, etc. In a scenario where the healthcare data corresponds to the patient record data, the one or more physiological parameters correspond to an m-dimensional variable and the number of records in the healthcare data corresponds to "n" observations.

A "data view" refers to a multivariate dataset associated with a particular data collection use case that may be obtained from a particular data source. A multi-view dataset may include a collection of plurality of data views that may be acquired from multiple data sources. For instance, the healthcare dataset may correspond to a multi-view data set. Examples of the plurality of data views associated with the historical data in the healthcare dataset may include, but are not limited to, a physiological-parameter data view, a demographic-details data view, a social-behavior data view, and/or a past-addictions data view.

A "human subject" corresponds to a human being, who may have a health condition or a disease. In an embodiment, the human subject may correspond to a person who seeks a medical opinion on his/her health condition.

A "data-acquisition (DAQ) device" refers to a device that may gather signals from an external stimulus and generate an output usable through a computing device for further processing. For example, the DAQ device may correspond to a temperature sensor that measures a surface temperature of a substrate and generates a corresponding temperature reading for further processing by a computing device.

A "DAQ interface" refers to an interface that facilitates communication between a DAQ device and a computing device. In an embodiment, to facilitate communication between a DAQ device and a computing device connected through the DAQ interface, the DAQ interface may convert a signal (that is in a first format) generated by the DAQ device to a signal (that is a second format) acceptable by the computing device, and vice versa. For instance, the DAQ interface may convert analog signals generated by a DAQ device to corresponding digital signals acceptable by a computing device. Further, the DAQ interface may serialize or parallelize the digital signals in accordance with data-input requirements of the computing device. Examples of the DAQ interface include, but are not limited to, a universal serial bus (USB) port, a FireWire Port, an IEEE 1394 standard based connector, or any other serial/parallel data interfacing connector known in the art.

"Biosensor" refers to a DAQ device that can be used to measure one or more physiological parameters of a human subject. Examples of a biosensor include, but are not limited to, a pressure/pulse sensor (to measure blood pressure and heart rate), a temperature sensor (to measure body temperature), a blood sample analyzer (to measure readings of various blood tests such as blood creatinine level, blood albumin level, blood sodium level, total blood count, blood glucose/sugar level, blood hemoglobin level, blood platelet count, and cholesterol level), a breath analyzer (to measure the carbon dioxide/oxygen concentration), and so on.

A "copula" refers to a multivariate probability distribution of a multivariate dataset, which may be used to decouple dependencies among various dimensions of the multivariate dataset. In an embodiment, the copula may be represented as a function of constituent univariate marginal distributions of the various dimensions in the multivariate dataset. In an embodiment, the univariate marginal distributions may be uniformly distributed. In an embodiment, an m-dimensional copula may be represented as a multivariate distribution function C: $[0, 1]^m \rightarrow [0,1]$. The following equation (1) represents a relationship between a joint distribution function F and the univariate marginal distributions $F_1(X_1)$, $F_2(X_2)$, ... $F_m(X_m)$ of an m-dimensional multivariate dataset, using an m-dimensional Copula function C:

$$F(X_1, X_2, \ldots X_m) = C(F_1(X_1), F_2(X_2), \ldots F_m(X_m)) \quad (1)$$

where, $X_i$: a random variable for the $i^{th}$ dimension of the m-dimensional multivariate dataset (e.g., a measure of a physiological parameter in a multivariate healthcare dataset);

$F_i(X_i)$: a univariate marginal distribution for the $i^{th}$ dimension of the m-dimensional multivariate dataset, where $U_i \leq F_i(X_i)$, $U_i$ is a cumulative distribution of $X_i$;

F( ): a joint distribution function of the m-dimensional multivariate dataset; and C( ): an m-dimensional copula function.

A "joint density function" refers to a joint probability distribution of a multivariate dataset. In an embodiment, the joint density function may represent a probability of assigning values to various dimensions of the multivariate dataset within a respective range associated with each dimension. In an embodiment, a joint density function $f$ of an m-dimensional multivariate dataset may be expressed in terms of an m-dimensional copula density function $c_{1 \ldots m}$ and univariate marginal density functions $f_1, f_2, \ldots f_m$, represented by equation (2), as follows:

$$f(X_1, X_2, \ldots X_m) = c_{1 \ldots m}(F_1(X_1), F_2(X_2), \ldots F_m(X_m)) \cdot f_1(X_1) \cdot f_2(X_2) \ldots f_m(X_m) \quad (2)$$

where, $f( )$: a joint density function of the m-dimensional multivariate dataset;

$f_i(X_i)$: a marginal density function of $X_i$; and $c_{1 \ldots m}$: an m-dimensional copula density function, represented by equation (3), as follows:

$$c_{1 \ldots m}(F_1(X_1), F_2(X_2), \ldots F_m(X_m)) = \frac{\delta C}{\delta F_1 \delta F_2 \ldots \delta F_m} C(F_1(X_1), F_2(X_2), \ldots F_m(X_m)) \quad (3)$$

In an embodiment, the joint density function $f$ of the m-dimensional multivariate dataset may also be expressed in terms of the conditional densities of the random variables, represented by equation (4), as follows:

$$f(X_1, X_2, \ldots X_m) = f_m(X_m) \cdot f(X_{m-1}|X_m) \ldots f(X_1|X_2, \ldots X_m) \quad (4)$$

where, $f(X_l|X_{l+1}, \ldots X_{l+j-1})$: a conditional density of the random variable $X_i$ (for the $i^{th}$ dimension), where $1 \leq l \leq m-1$ and $j=m-l$.

By simplifying the equations (2) and (4), the joint density function $f$ may be expressed in terms of univariate marginal density functions $f_1, f_2, \ldots f_m$ and bivariate copula densities, represented by equation (5), as follows:

$$f(X_1, X_2, \ldots X_m) = \Pi_{k=1}^m f_k(X_k) \Pi_{j=1}^{m-1} \Pi_{l=1}^{m-j} c_{l,l+j|l+1, \ldots l+j-1}(F(X_l|X_{l+1}, \ldots X_{l+j-1}), F(X_{l+j}|X_{l+1}, \ldots X_{l+j-1})) \quad (5)$$

where, $c_{l,l+j|l+1, \ldots l+j-1}$: a density of a bivariate copula distribution $C_{l,l+j|l+1, \ldots l+j-1}$; and $F(X_l|X_{l+1}, \ldots X_{l+j-1})$: a conditional cumulative distribution of the random variable $X_i$.

A "bivariate copula distribution" refers to a copula distribution that may model a dependency between a pair of dimensions of a multivariate dataset. Examples of the bivariate copula distribution may include, but are not limited to, a T-student copula distribution, a Clayton copula distribution, a Gumbel copula distribution, or a Gaussian copula distribution, which are known in the art. In an embodiment, the bivariate copula distribution may be a part of a D-vine copula distribution.

A "D-vine copula" refers to a hierarchal collection of bivariate copula distributions. In an embodiment, the D-vine copula may be represented graphically by a set of hierarchal trees, each of which may include a set of nodes arranged sequentially and connected by a set of edges. Further, each edge, connecting a pair of nodes in a hierarchal tree, may represent a bivariate copula distribution. In an embodiment, for "m" random variables, the D-vine copula may correspond to a hierarchal structure that includes m-1 hierarchal trees, representing a total of $$\frac{m(m-1)}{2}$$

bivariate copula distributions. For example, a D-vine copula may be used to represent the bivariate copula distributions of the equation (5). In such a scenario, the variable j in the equation (5) may identify a hierarchal tree of the D-vine copula and the variable l in the equation (5) may identify an edge within that hierarchal tree for representing each bivariate copula distribution of the equation (5) through the D-vine copula. In an embodiment, the D-vine copula may model a dependency between each pair of dimensions in a multivariate dataset. In an embodiment, the constituent bivariate copula distributions within the D-vine copula model may belong to different families of copula functions. Each such bivariate copula distribution within a D-vine copula model is interchangeably hereinafter referred as a D-vine pair copula family. Examples of the various families of copula functions that may be used as a D-vine pair copula family include, but are not limited to, a T-student copula distribution, a Clayton copula distribution, a Gumbel copula distribution, or a Gaussian copula distribution.

A "D-vine mixture model" refers to a semi-parametric D-vine copula model that may distribute data into multiple clusters, such that data in each cluster may be modeled using a D-vine pair copula family selected from a set of candidate D-vine pair copula families. The D-vine pair copula family used to model data distributed in a cluster may be selected based on a best-fit criterion. Thus, a D-vine mixture model may correspond to a D-vine copula model, in which data may be segregated into various clusters, each of which may be modeled using an appropriate D-vine pair copula family within the D-vine copula model. The D-vine mixture model may be useful to detect data dependency across different data views and data dependency within a single data view. Thus, inter-data view and intra-data view dependency structures may be determined using a D-vine mixture model.

An "h-function" refers to a conditional distribution of a random variable in terms of a bivariate copula distribution with known parameters. In an embodiment, the h-function may be used to represent an m-dimensional conditional distribution in terms of a pair of (m-1)-dimensional conditional distributions. Thus, the h-function may be used to recursively evaluate a conditional distribution in terms of individual random variables representing the various dimensions of the original conditional distribution. The following is a generic expression of a conditional cumulative distribution function represented in terms of an h-function, shown through an equation (6), as follows:

$$F(X_j | X_1, \ldots X_{j-1}) = \frac{\delta C_{j,1|2, \ldots j-1}(F(X_j | X_2, \ldots X_{j-1}), F(X_1 | X_2, \ldots X_{j-1}))}{\delta F(X_1 | X_2, \ldots X_{j-1})} = h(F(X_j | X_2, \ldots X_{j-1}), F(X_1 | X_2, \ldots X_{j-1}); \sum_{j,1|2 \ldots j-1}) \quad (6)$$

where, $F(X_j|X_1, \ldots X_{j-1})$: a conditional cumulative distribution of $X_j$;

$C_{j,1|2, \ldots j-1}$: a bivariate copula distribution between $j^{th}$ and $1^{st}$ dimensions, conditioned on $2^{nd}, 3^{rd}, \ldots (j-1)^{th}$ dimensions;

$\Sigma_{j,1|2 \ldots j-1}$: parameters of the bivariate copula distribution $C_{j,1|2, \ldots j-1}$, which may be pre-estimated; and h( ): h function.

A person skilled in the art will understand that a conditional cumulative distribution of a random variable may be equivalent to a conditional cumulative distribution of the corresponding marginal distribution of the random variable. Hence, an h-function in terms of the random variable may be equivalent to an h-function in terms of the corresponding marginal distribution of the random variable. For instance, $X_1$ and $X_2$ are random variables with corresponding marginal distributions $U_1=F_1(X_1)$ and $U_2=F_2(X_2)$. Then, $F(U_1/U_2)=F(X_1/X_2)=h(X_1,X_2)=h(U_1,U_2)$.

A "cumulative distribution" refers to a distribution function, which describes the probability that a real-valued random variable X, with a given probability distribution, will be found at a value less than or equal to a threshold value.

A "marginal cumulative distribution" refers to a cumulative distribution of a random variable representing a single dimension of a multivariate dataset. For example, $X_i$ is a random variable representing an $i^{th}$ dimension of the multivariate dataset. The marginal cumulative distribution of $X_i$ may be represented as $F_i(X_i)$ or $U_i$.

A "conditional cumulative distribution" refers to a multivariate cumulative distribution of multiple random variables, which is conditioned on at least one of the random variable. For example, $F(X_3/X_2, X_1)$ is a three-dimensional conditional cumulative distribution of random variables $X_1$, $X_2$, and $X_3$, such that the marginal cumulative distribution of the random variable $X_3$ may be conditioned on the marginal cumulative distributions of the random variables $X_1$ and $X_2$.

An "inverse cumulative distribution" refers to an inverse function of the cumulative distribution of the random variable X.

A "latent variable" refers to an intermediate or a transient variable that may not be directly obtainable from a multivariate dataset. In an embodiment, the latent variable may be determined based on one or more parameters of a distribution representing the multivariate dataset. For example, a latent variable (e.g., U) may be determined based on a marginal cumulative distribution (e.g., $F_i(X_i)$) of each dimension (e.g., $X_i$) in the multivariate dataset.

"Probability" refers to a likelihood of the occurrence of an event. In an embodiment, probability may correspond to a ratio of favorable outcomes to total number of possible outcomes related to the event. The term "probability" shall be broadly construed to include any calculation of probability; approximation of probability, using any type of input data, regardless of precision or lack of precision; any number, either calculated or predetermined, that simulates a probability; or any method step having an effect of using or finding some data that has some relation to a probability.

A "random variable" refers to a variable that may be assigned a value probabilistically or stochastically.

A "classifier" refers to a mathematical model that may be configured to categorize data into one or more categories. In an embodiment, the classifier is trained based on historical data. Examples of the classifier may include, but are not limited to, a support vector machine (SVM), a logistic regression, a Bayesian classifier, a decision tree classifier, a Copula-based classifier, a K-nearest neighbors (KNN) classifier, or a random forest (RF) classifier.

"Training" refers to a process of updating/tuning a classifier using historical data, such that the classifier is able to predict one or more categories in the historical data with a greater accuracy.

"Gibbs sampling" refers to a statistical technique that may be used to generate samples from a multivariate distribution. In an embodiment, Gibbs sampling corresponds to a Markov Chain Monte Carlo (MCMC) algorithm that works to obtain a sequence of observations from a joint distribution of two or more univariate marginal distributions when direct sampling from the multivariate distribution may be difficult.

"Expectation Maximization (EM) algorithm" refers to a statistical technique of determining a maximum likelihood estimate (MLE) of one or more parameters of a distribution, where the distribution depends on unobserved latent variables.

FIG. 1 is a block diagram, illustrating a system environment in which various embodiments may be implemented in accordance with at least one embodiment. With reference to FIG. 1, a system environment 100 is shown. The system environment 100 includes an application server 102, a database server 104, a human-subject computing device 106, a set of biosensors 108, a set of DAQ interfaces 110, a multi-view dataset 112 including data from multiple data sources, and a communication network 114. The set of DAQ interfaces 110 includes a DAQ interface_1 110a, a DAQ interface_2 110b, and a DAQ interface_3 110c, while the set of biosensors 108 includes a biosensor_1 108a, a biosensor_2 108b, and a biosensor_3 108c. The multi-view dataset 112 includes multiple data views such as DS_1 112a, DS_2 112b, DS_3 112c, and a DS_4 112d.

The application server 102 refers to a computing device, including one or more processors and one or more memory units. The one or more memory units may include computer readable code that is executable by the one or more processors to perform predetermined operations. In an embodiment, the predetermined operations may include data processing to predict a health condition of a human subject. In an embodiment, the application server 102 may extract historical data, comprising medical records of one or more first human subjects, from the database server 104 over the communication network 114. In an embodiment, the historical data may include a medical record associated with a human subject. The medical record may include a measure of one or more physiological parameters associated with the human subject. The medical record of the human subject may also include other information associated with the human subject. In an embodiment, the historical data may correspond to the multi-view dataset 112. Thus, each medical record in the historical data may include data that may correspond to multiple data views, such as the data views DS_1 112a, DS_2 112b, DS_3 112c, and DS_4 112d. Examples of the multiple data views in the multi-view dataset 112 may include, but are not limited to, a physiological-parameter data view, a demographic-details data view, a social-behavior data view, and/or a past-addictions data view.

In an embodiment, for each of the multiple data views, the application server 102 may cluster data corresponding to the data view in the historical data into one or more clusters. The application server 102 may model each of the one or more clusters using a D-vine pair copula family associated with a D-vine mixture model. The D-vine pair copula family may be selected from one or more D-vine pair copula families based on the best-fit criteria to model the particular cluster. The clustering may be performed by sampling a plurality of latent variables based on a rank transformation of the historical data. Thereafter, for each of the multiple data views, the application server 102 may estimate one or more of the plurality of latent variables based on at least a first value, a second value, and a third value. The first value may be indicative of a count of the one or more records clustered in a cluster from the one or more clusters corresponding to the data view. The second value may be indicative of a count of the one or more medical records. The third value may be indicative of a parameter that may be utilized to predict a fourth value. The fourth value may correspond to a probability of selection of the D-vine pair copula family from the one or more D-vine pair copula families, to model the cluster from the one or more clusters corresponding to the data view. Further, the application server 102 may generate the D-vine mixture model, including the D-vine pair copula family selected for each of the plurality of data views, based on the estimated one or more of the plurality of latent variables. After the generation of the D-vine mixture model, the application server 102 may train a classifier based on the generated D-vine mixture model. The training of the classifier based on the D-vine mixture model has been explained further in conjunction with FIG. 3.

In an embodiment, the application server 102 may receive multi-view data associated with a second human subject from one or more data sources (such as the multi-view dataset 112) or the human-subject computing device 106 over the communication network 114. The application server 102 may be configured to predict a health condition of the second human subject by utilizing the trained classified based on the received multi-view data associated with the second human subject. The application server 102 may then transmit the predicted health condition of the second human subject to one or more computing devices, such as the human-subject computing device 106 of the second human subject. The predicted health condition of the second human subject may then be presented to the second human subject through a user-interface on the human-subject computing device 106. The prediction of the health condition of the second human subject has been explained further in conjunction with FIG. 4.

The application server 102 may be realized through various types of application servers such as, but not limited to, Java application server, .NET framework application server, and Base4 application server.

The database server 104 may refer to a computing device, which stores at least the historical data, including the medical records of the one or more first human subjects. In an embodiment, data stored in the database server 104 may also include the multi-view data of the second human subject, received from the human-subject computing device 106 of the second human subject and/or one or more other data sources (not shown in FIG. 1). In an embodiment, the data stored in the database server 104 may correspond to the multi-view dataset 112, including the data views DS_1 112*a*, DS_2 112*b*, DS_3 112*c*, and DS_4 112*d*. For instance, the data view DS_1 112*a* may correspond to a physiological-parameter data view and may include a measure of one or more physiological parameters of one or more human subjects that may be received from the human-subject computing device 106 of each human subject. The measure of the one or more physiological parameters of a human subject may be measured by a biosensor (e.g., the biosensor_1 108*a*) and transferred to the human-subject computing device 106 associated with the human subject via a corresponding DAQ interface (e.g., the DAQ interface_1 110*a*). In an embodiment, the other data views DS_2 112*b*, DS_3 112*c*, and DS_4 112*d* may correspond to a demographic-details data view, a social-behavior data view, and/or a past-addictions data view, respectively. The database server 104 may receive data views DS_2 112*b*, DS_3 112*c*, and DS_4 112*d* of one or more human subjects from other data sources associated with the one or more human subjects. A person skilled in the art will understand that the aforementioned data views are for exemplary purposes and should not be construed to limit the scope of the disclosure.

In an embodiment, the database server 104 may receive a query from the application server 102 to extract the information stored on the database server 104. The database server 104 may be realized through various technologies such as, but not limited to, Oracle®, IBM DB2®, Microsoft SQL Server®, Microsoft Access®, PostgreSQL®, MySQL®, and SQLite®, and the like. In an embodiment, the application server 102 may connect to the database server 104 using one or more protocols such as, but not limited to, Open Database Connectivity (ODBC) protocol and Java Database Connectivity (JDBC) protocol.

A person with ordinary skill in the art will understand that the scope of the disclosure is not limited to the database server 104 as a separate entity. In an embodiment, the functionalities of the database server 104 can be integrated into the application server 102.

The human-subject computing device 106*l* refers to a computing device used by a human subject (such as the one or more first human subjects and/or the second human subject). The human-subject computing device 106 may include one or more processors and one or more memory units. The one or more memory units may include computer-readable code that is executable by the one or more processors to perform predetermined operations. In an embodiment, the set of biosensors 108 may be inbuilt within the human-subject computing device 106. Alternatively, the set of biosensors 108 may be communicatively coupled to the human-subject computing device 106 through the set of DAQ interfaces 110. For instance, as shown in FIG. 1, the DAQ interface_1 110*a* may connect the biosensor_1 108*a* with the human-subject computing device 106. Similarly, the DAQ interface_2 110*b* may connect the biosensor_2 108*b* with the human-subject computing device 106, and so on. In another embodiment, the set of biosensors 108 may be connected to the human-subject computing device 106 through a wireless connection such as, but not limited to, a Bluetooth-based connection, a near field communication (NFC)-based connection, a radio frequency identification (RFID)-based connection, or any other wireless communication protocol.

In an embodiment, the set of biosensors 108 may refer to DAQ devices that can be used to gather various signals from a human subject and generate corresponding readings of the one or more physiological parameters of the human subject. Examples of the one or more physiological parameters include, but are not limited to, age, cholesterol level, heart rate, blood pressure, breath carbon dioxide concentration, breath oxygen concentration, stroke score, blood creatinine level, blood albumin level, blood sodium level, total blood count, blood glucose/sugar level, blood hemoglobin level, and blood platelet count. In an embodiment, the set of biosensors 108 may be attached to a body of the human subject to measure the one or more physiological parameters of the human subject. Examples of such biosensors include, but are not limited to, a blood pressure/pulse sensor, or a temperature sensor. Alternatively, the set of biosensors 108 may correspond to one or more blood sample analyzers for analyzing a blood sample taken from the human subject to determine readings of one or more blood tests. In another embodiment, the set of biosensors 108 may correspond to one or more breath-analyzers for analyzing a breath sample of the human subject.

In an embodiment, the set of DAQ interfaces 110 may connect the set of biosensors 108 with the human-subject computing device 106. Further, the set of DAQ interfaces 110 may facilitate communication between the set of biosensors 108 and the human-subject computing device 106. In an embodiment, a corresponding DAQ interface (e.g., the DAQ-interface_1 110*a*) between a biosensor (e.g., the biosensor-1 108*a*) and the human-subject computing device 106 may facilitate communication between the biosensor (e.g., the bio-sensor-1 108*a*) and the human-subject computing device 106. The DAQ interface (e.g., the DAQ-interface_1 110*a*) may convert a signal (in a first format) generated by the biosensor (e.g., the bio-sensor-1 108*a*) to a signal (in a second format) acceptable by the human-subject computing device 106, and vice versa, to facilitate their communication. For instance, a DAQ interface (e.g., the DAQ-interface_1 110*a*) may convert analog signals generated by a biosensor (e.g., the biosensor_1 108*a*) to corresponding digital signals acceptable by the human-subject computing device 106. Further, a DAQ interface (e.g., the DAQ interface_1 110*a*) may serialize or parallelize the digital signals in accordance with data-input requirements of the human-subject computing device 106. For instance, the DAQ interface (e.g., the DAQ interface_1 110*a*) may parallelize digital signals into 32-bit data words if the human-subject computing device 106 accepts digital data in a 32-bit format. Examples of the DAQ interface include, but are not limited to, a USB port, a FireWire port, an IEEE 1394 standard based connector, or any other serial/parallel data interfacing connector known in the art. A person skilled in the art will understand that the aforementioned DAQ interfaces and biosensors are for exemplary purposes and should not be construed to limit the scope of the disclosure.

In an embodiment, the human-subject computing device 106 may transmit the measure of the one or more physiological parameters of the human subject to at least one of the application server 102 or the database server 104. The measure of the one or more physiological parameters of the human subject may be stored in the data view DS_1 112a. Further, the human subject or a medical practitioner associated with the human subject may provide other details related to the human subject, such as demographic information, observations related to social behavior of the human subject, and details related to past addictions of the human subject. The human subject or the medical practitioner associated with the human subject may use their respective computing devices (e.g., the human-subject computing device 106 or a medical-practitioner computing device (not shown in FIG. 1)) to provide the other details. The aforementioned details related to the human subject may be stored in the data views such as DS_2 112b, DS_3 112c, and DS_4 112d. In an embodiment, the application server 102 may predict a health condition of the human subject, as described above. Thereafter, the human-subject computing device 106 may display the predicted health condition of the human subject through a user interface on a display device of the human-subject computing device 106 (or a medical practitioner computing device). Based on the predicted health condition of the human subject, the human subject may consult the medical practitioner.

A person skilled in the art will understand that the scope of the disclosure is not limited to the human-subject computing device 106 being used by the human subject. In an embodiment, the human-subject computing device 106 may be used by a medical practitioner. In such a scenario, when a human subject visits the medical practitioner for a consultation, the medical practitioner may use the human-subject computing device 106 to measure the one or more physiological parameters of the human subject. Thereafter, the human-subject computing device 106 may transmit the one or more physiological parameters of the human subject to at least one of the application server 102 and/or the database server 104. Further, the other details related to the human subject may also be provided through the user interface of the human-subject computing device 106 for transmission to the application server 102 and/or the database server 104. The application server 102 may predict a health condition of the human subject, as described above. In an embodiment, the health condition may correspond to at least one of a mortality risk, a disease risk, a disease symptom, an onset of a disease, a recovery from a disease, or an effect of medications for a disease. Thereafter, the human-subject computing device 106 may display the predicted health condition of the human subject through the user interface on a display device of the human-subject computing device 106. Based on the predicted health condition of the human subject, the medical practitioner may recommend a treatment course, including one or more medicines, one or more clinical/pathological tests, or one or more diet plans to the human subject.

The human-subject computing device 106 may include a variety of computing devices such as, but not limited to, a laptop, a personal digital assistant (PDA), a tablet computer, a smartphone, a phablet, and the like.

A person skilled in the art will understand that the scope of the disclosure is not limited to the human-subject computing device 106 and the application server 102 as separate entities. In an embodiment, the application server 102 may be realized as an application hosted on, or running on, the human-subject computing device 106 without departing from the spirit of the disclosure.

The communication network 114 corresponds to a medium through which content and messages flow between various devices of the system environment 100 (e.g., the application server 102, the database server 104, and the human-subject computing device 106). Examples of the communication network 114 may include, but are not limited to, a Wireless Fidelity (Wi-Fi) network, a Wireless Area Network (WAN), a Local Area Network (LAN), or a Metropolitan Area Network (MAN). Various devices in the system environment 100 can connect to the communication network 114 in accordance with various wired and wireless communication protocols such as Transmission Control Protocol and Internet Protocol (TCP/IP), User Datagram Protocol (UDP), and 2G, 3G, LTE, LTE-Advanced (4G), or 5G communication protocols.

Figure 2:
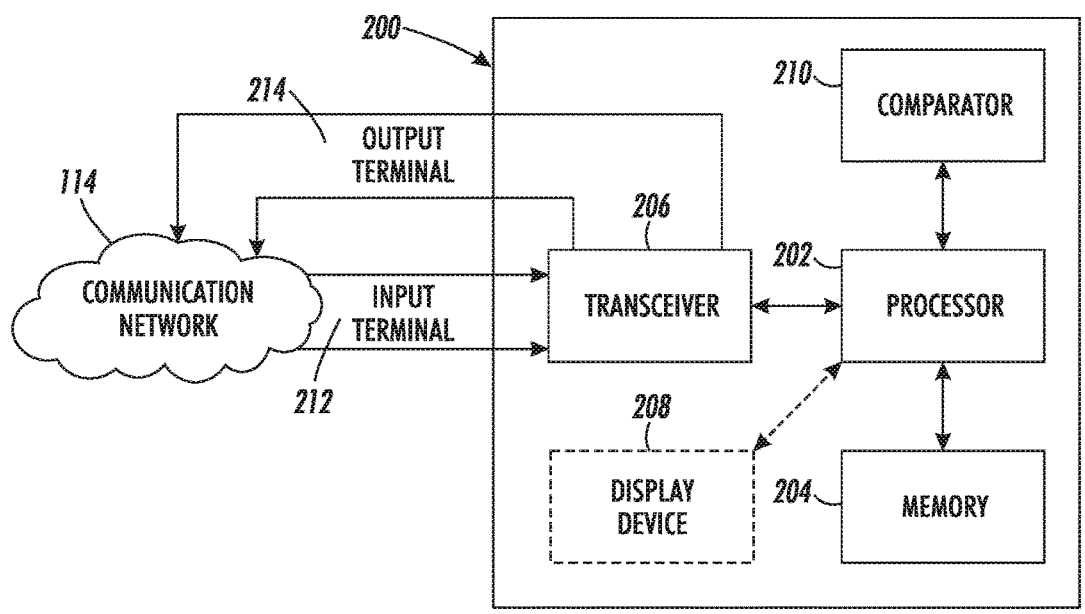
FIG. 2 is a block diagram of a system that predicts health condition of a human subject, in accordance with at least one embodiment.

FIG. 2 is a block diagram of a system that predicts health condition of a human subject, in accordance with at least one embodiment. FIG. 2 is explained in conjunction with FIG. 1. With reference to FIG. 2, there is shown a system 200 (a computing device) that may correspond to the application server 102 or the human-subject computing device 106. For the purpose of ongoing description, the system 200 is considered to correspond to the application server 102. However, the scope of the disclosure should not be limited to the system 200 as the application server 102. The system 200 may also be realized as the human-subject computing device 106, without departing from the spirit of the disclosure.

The system 200 includes a processor 202, a memory 204, a transceiver 206, a display device 208, and a comparator 210. The processor 202 is coupled to the memory 204 and the transceiver 206. The transceiver 206 is coupled to the communication network 114 through an input terminal 212 and an output terminal 214.

The processor 202 includes suitable logic, circuitry, and interfaces and is configured to execute one or more instructions stored in the memory 204 to perform predetermined operations on the system 200. The memory 204 may be configured to store the one or more instructions. The processor 202 may be implemented using one or more processor technologies known in the art. Examples of the processor 202 include, but are not limited to, an X86 processor, a RISC processor, an ASIC processor, a CISC processor, or any other processor.

In an embodiment, the predetermined operations may include data processing to predict a health condition of a human subject. In an embodiment, the processor 202 may be configured to extract historical data, comprising medical records of one or more first human subjects, from the database server 104. In an embodiment, the historical data may correspond to the multi-view dataset 112. Thus, each medical record in the historical data may include data that may correspond to multiple data views, such as the data views DS_1 112a, DS_2 112b, DS_3 112c, and DS_4 112d. In an embodiment, for each of the multiple data views, the processor 202 may be configured to cluster data, corresponding to the data view in the historical data, into one or more clusters. Each of the one or more clusters may then be modeled using a D-vine pair copula family associated with a D-vine mixture model. The D-vine pair copula family may be selected from one or more D-vine pair copula families based on best fit criteria to model the particular cluster. The clustering may be performed by sampling of a plurality of latent variables based on a rank transformation of the historical data. The processor 202 may be configured to then estimate one or more of the plurality of latent variables based on at least a first value, a second value, and a third value, for each of the multiple data views. Further, the processor 202 may be configured to generate the D-vine mixture model including the D-vine pair copula family selected for each of the plurality of data views, based on the estimated one or more of the plurality of latent variables. After the generation of the D-vine mixture model, the processor 202 may train a classifier based on the generated D-vine mixture model.

In an embodiment, the processor 202 may be configured to receive multi-view data associated with a second human subject from one or more data sources (such as the multi-view dataset 112) or the human-subject computing device 106 over the communication network 114, via the transceiver 206. The processor 202 may be configured predict a health condition of the second human subject in real-time by utilizing the trained classified based on the received multi-view data associated with the second human subject. The processor 202 may then transmit the predicted health condition of the second human subject to one or more computing devices, such as the human-subject computing device 106 of the second human subject.

The memory 204 stores a set of instructions and data. Further, the memory 204 includes the one or more instructions that are executable by the processor 202 to perform specific operations. Some of the commonly known memory implementations include, but are not limited to, a RAM, a read-only memory (ROM), a hard disk drive (HDD), and a secure digital (SD) card. It is apparent to a person having ordinary skill in the art that the one or more instructions stored in the memory 204 enable the hardware of the system 200 to perform the predetermined operations.

The transceiver 206 transmits and receives messages and data to/from one or more computing devices connected to the system 200 over the communication network 114. Examples of the communication network 114 may include, but are not limited to, a Wireless Fidelity (Wi-Fi) network, a Wireless Area Network (WAN), a Local Area Network (LAN), or a Metropolitan Area Network (MAN). In an embodiment, the transceiver 206 is coupled to the communication network 114 through the input terminal 212 and the output terminal 214, through which the transceiver 206 may receive and transmit data/messages respectively. Examples of the transceiver 206 may include, but are not limited to, an antenna, an Ethernet port, a USB port, or any other port that can be configured to receive and transmit data. The transceiver 206 transmits and receives data/messages in accordance with the various communication protocols such as, TCP/IP, UDP, and 2G, 3G, LTE, LTE-Advanced (4G), or 5G communication protocols.

The display device 208 facilitates a user of the system 200 to view information presented on the system 200. For example, the user may view information associated with the predicted health condition of a human subject on the display device 208. The display device 208 may be realized through several known technologies, such as Cathode Ray Tube (CRT) based display, Liquid Crystal Display (LCD), Light Emitting Diode (LED) based display, Organic LED based display, and Retina Display® technology. In an embodiment, the display device 208 can be a touch screen that is operable to receive a user-input.

The comparator 210 is configured to compare at least two input signals to generate an output signal. In an embodiment, the output signal may correspond to either "1" or "0." In an embodiment, the comparator 210 may generate output "1" if the value of a first signal (from the at least two signals) is greater than the value of a second signal (from the at least two signals). Similarly, the comparator 210 may generate an output "0" if the value of the first signal is less than the value of the second signal. In an embodiment, the comparator 210 may be realized through either software technologies or hardware technologies known in the art. Though, the comparator 210 is depicted as independent from the processor 202 in FIG. 2, a person skilled in the art will appreciate that the comparator 210 may be implemented within the processor 202 without departing from the scope of the disclosure.

Figure 3:
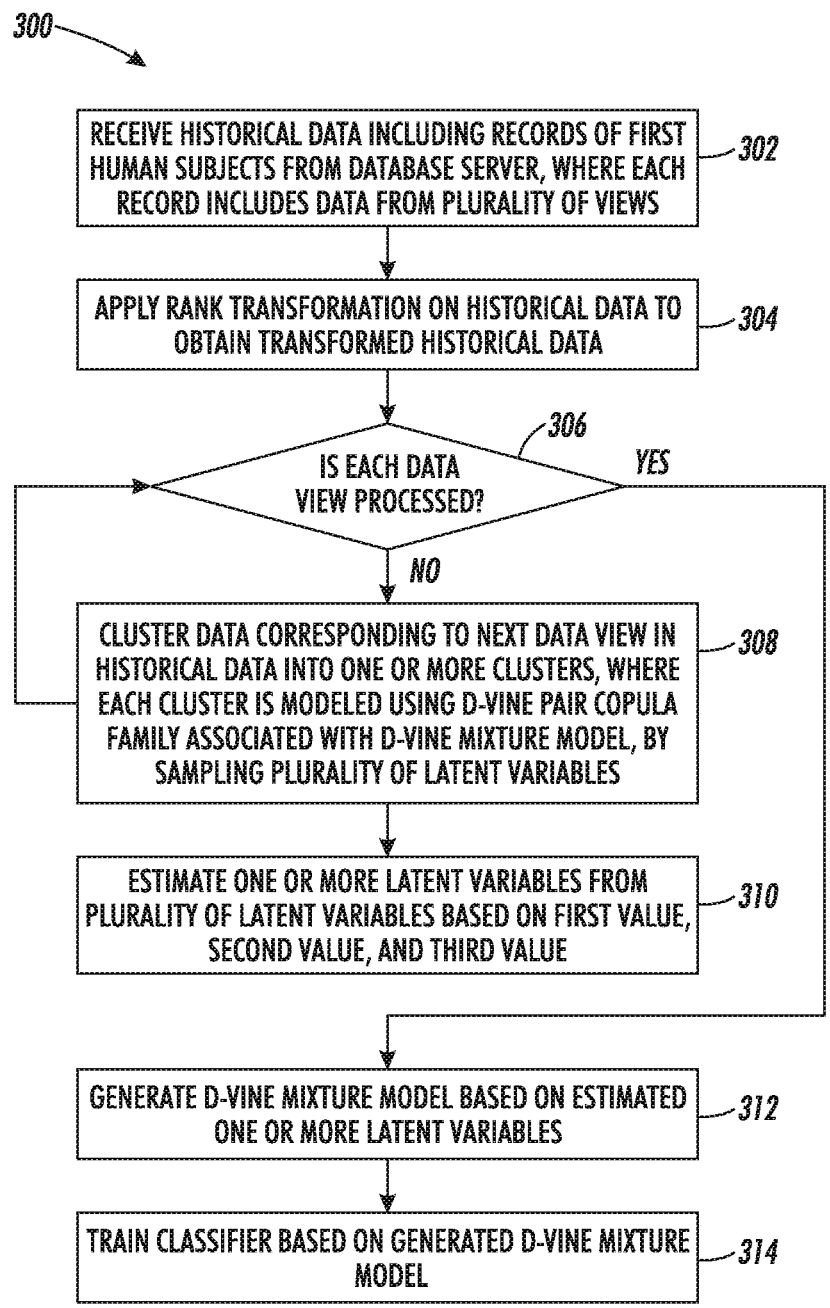
FIG. 3 illustrates a flowchart of a method to train a classifier based on generation of a D-vine mixture model, in accordance with at least one embodiment.

An embodiment of operation of the system 200 for training of the classifier based on the generation of a D-vine mixture model has been explained further in conjunction with FIG. 3. The prediction of a health condition of a human subject using the trained classifier has been explained in conjunction with FIG. 4.

FIG. 3 illustrates a flowchart of a method to train a classifier based on the generation of a D-vine mixture model, in accordance with at least one embodiment. With reference to FIG. 3, there is shown a flowchart 300 that has been described in conjunction with FIG. 1 and FIG. 2.

At step 302, the historical data, including medical records of the one or more first human subjects, is extracted. In an embodiment, the processor 202 is configured to extract the historical data from the database server 104. In a scenario where the historical data is stored in the memory 204, the processor 202 may extract the historical data from the memory 204. In an embodiment, the historical data may correspond to a multivariate dataset from which the health condition of a human subject may be identifiable based on the generation of a D-vine mixture model. Further, the data type associated with the historical data corresponds to at least one of a numerical data type or a categorical data type.

In an embodiment, each medical record in the historical data may correspond to an observation in an M-dimensional multivariate dataset corresponding to the historical data. Further, the historical data may correspond to multiple data views, each of which may include a multivariate healthcare dataset. Thus, the M-dimensional multivariate dataset within historical data may include a collection of multivariate datasets associated with each of the multiple data views. For instance, the historical data may include the multi-view dataset 112, such as a physiological data view (e.g., the DS_1 112*a*), a demographic details data view (e.g., the DS_2 112*b*), a social behavior data view (e.g., the DS_3 112*c*), and a past addictions data view (e.g., the DS_4 112*d*). The physiological parameters data view (e.g., the DS_1 112*a*) may include a measure of one or more physiological parameters of each of the one or more first human subjects. The measure of each of the one or more physiological parameters may together correspond to a multivariate dataset associated with the physiological parameter data view (e.g., the DS_1 112*a*) within the historical data. Examples of the one or more physiological parameters of a human subject may include, but are not limited to, age, cholesterol level, heart rate, blood pressure, breath carbon dioxide concentration, breath oxygen concentration, stroke score, blood creatinine level, blood albumin level, blood sodium level, total blood count, blood glucose/sugar level, blood hemoglobin level, and blood platelet count of the human subject. A person skilled in the art will understand that the scope of disclosure is not limited to the aforementioned one or more physiological parameters. In an embodiment, various other physiological parameters may be considered without departing from the spirit of the disclosure. Further, the aforementioned data views are enumerated for exemplary purposes and should not be construed to limit the scope of the disclosure.

At step 304, a rank transformation is applied on the historical data to obtain a transformed historical data. In an embodiment, the processor 202 is configured to obtain the transformed historical data by applying the rank transformation on the historical data using an extended rank likelihood technique. To generate the transformed historical data, the processor 202 may determine ranks of the individual observations in each dimension in the historical data. In an embodiment, the processor 202 may assign a rank "1" to an observation having the highest value among the other observations in a particular dimension. Further, the processor 202 may assign a rank "2" to an observation having the next highest value in that dimension, and so on until a rank "N" is assigned to an observation having the lowest value in the particular dimension in the historical data. Thereafter, in an embodiment, the processor 202 may normalize the ranks based on the division of each rank by "N" so that the final values of the ranks of the observations lie between "0" and "1." The final values of the ranks of the observations, which lie between "0" and "1," may correspond to the transformed historical data. For example, the historical data includes five observations. The values of the five observations for a particular dimension may include the values "0.1," "5.6," "3.1," "0.8," and "2.2." The processor 202 may assign the ranks "1," "5," "4," "2," and "3" to the observations, respectively. Further, the processor 202 may determine the final values of the ranks, and hence the transformed historical data, as "0.2," "1," "0.8," "0.4," and "0.6" (i.e., by dividing the ranks by "5").

A person skilled in the art will appreciate that the historical data may include data of various data types such as, but not limited to, a numerical data type or a categorical data type. For instance, a first set of dimensions in the historical data may include data of a continuous data type, while a second set of dimensions in the historical data may include data of a discrete data type. However, in an embodiment, the transformed historical data may include only the ranks. Further, the transformed historical data may not have any missing values, even in a scenario where the historical data has certain missing values. In an embodiment, a bivariate copula distribution (or a D-vine pair copula family) determined from the original historical data may be the same as a bivariate copula distribution (or a D-vine pair copula family) determined from the transformed historical data. As the transformed multivariate dataset does not include any missing values or categorical data, the bivariate copula distribution (or a D-vine pair copula family) determined from the transformed historical data may more accurately model one or more clusters in the historical data.

For example, the historical data includes a physiological parameter, such as "Gender," which is of a categorical data type. Thus, observations for the physiological parameter "Gender" may have either a value of "Male" or "Female," which in turn may be represented as "0" and "1" in the historical data. In an embodiment, the processor 202 may determine a binomial distribution of the observations of gender in the historical data. Thereafter, the processor 202 may fit the binomial distribution to a Gaussian distribution based on the rank transformation. Thus, the observations of categorical data type in the historical data may be converted into numerical data in the transformed historical data. Further, a missing value $u_{ij}$ in the historical data may be computed based on an inverse transform sampling of a random variable $X_j$ (for the $j^{th}$ physiological parameter). Inverse transform sampling of the random variable X has been explained in conjunction with Algorithm 2 below. The data corresponding to each data view in the historical data may be processed by clustering the data into one or more clusters using a D-vine pair copula family associated with a D-vine mixture model, as explained next.

At step 306, a check is performed to determine whether each of the multiple data views corresponding to the historical data has been processed by clustering the data of the data view. The comparator 210 or the processor 202 may perform the check of step 306. If it is determined that each data view has been processed, step 312 may be performed; otherwise step 308 may be performed for the next unprocessed data view corresponding to the historical data.

At step 308, data corresponding to the next unprocessed data view in the historical data may be clustered into one or more clusters. In an embodiment, the processor 202 is configured to cluster data corresponding to the next unprocessed data view in the historical data into one or more clusters. Each of the one or more clusters in which data of a data view is clustered may be modeled using a D-vine pair copula family associated with a D-vine mixture model. The D-vine pair copula family that may be used to model a cluster may be selected from one or more D-vine pair copula families based on a best-fit constraint. Multi-view clustering of data using D-vines is explained using a notational example.

Consider that the historical data is represented as $\{X_{i,v,j}\}$, data points collected from V data views represented as N, where i∈N data points, v∈V data views, and j∈M dimensions in the historical data. The number of dimensions associated with a specific data view v is denoted as $M_v$, such that a collection of number of dimensions of all the data views V is equal to the total number of dimensions in the historical data, which is M. Data from the rank-transformed historical data may be clustered simultaneously from all the data views, while intra-data view dependency in each data view may also be modeled at the same time. This may be accomplished by clustering data of each data view v in the rank-transformed historical data into one or more clusters (where each cluster is denoted by k). The number of clusters or mixture components used to cluster the data of the various data views may be determined based on a non-parametric Dirichlet Process (DP). Thereafter, each cluster may be modeled using an appropriate D-vine pair copula family associated with a D-vine mixture model by extending a generative model of a D-vine copula (as per equations (7a) and (7b)) with a DP mixture model (as per equations (8a) to (8g)), as follows:

$$\text{For each observation } \forall i=1, \ldots N; \ U_i \sim \text{DVine}_{Unif}(\Sigma, \Theta) \quad (7a)$$

$$\text{For each dimension } \forall j=1, \ldots M; \ X_{i,j}=F_j^{-1}(U_{i,j}) \quad (7b)$$

where, $U_i$: a latent variable that represents an M-dimensional marginal for each data point i (i.e., $U_i \in R^M$), which may be sampled from D-vine pair copula families with uniform marginals;

$\text{DVine}_{Unif}$: D-vine pair copula families with uniform marginals;

Σ: collection of parameters (such as covariance matrices) of all D-vine pair copula families represented by $DVine_{Unif}$, where size of Σ depends on the number of D-vine copula families;

Θ: set of bivariate copula families for each individual pair copula of the D-vine, such that $\Theta = \{\theta_{s,t}: 1 \le s < t \le M_v\}$ has $$\binom{M}{2}$$

parameters corresponding to $$\binom{M}{2}$$

bivariate copulas, each of which may take values from the set $\{1, \ldots T\}$ corresponding to the "T" chosen bivariate copula families;

s,t: indexes of the individual pair copula denoted by $C_{s,t/s+1,\ldots s+t-1}$;

$X_{i,j}$: observation from $j^{th}$ dimension of $i^{th}$ data point; and $F_j^{-1}(U_{i,j})$: inverse marginal cumulative distribution of the latent variable $U_{i,j}$ (for $j^{th}$ dimension of $i^{th}$ data point).

The extended generative model of the D-vine copula using the DP mixture model is explained next. The D-vine pair copula family used to model a cluster k associated with a data view v may be denoted as $\Theta = \{\Theta_{k,v}\}$, while corresponding parameters of the D-vine pair copula family may be denoted as $\Sigma = \{\Sigma_{k,v}\}$. Thus, the D-vine pair copula families for each cluster k and data view v may be represented as $\Theta_{k,v} = \{\theta_{k,v,s,t}: 1 \le s < t \le M_v\}$, while corresponding parameters of the D-vine pair copula families may be represented as $\Sigma_{k,v} = \{\sigma_{k,v,s,t}: 1 \le s < t \le M_v\}$. Here, $M_v$ corresponds to the number of dimensions in a data view v and the total number of clusters is equal to K. Further, s and t correspond to indexes of the pair copula denoted by $C_{s,t/s+1,\ldots s+t-1}$. The D-vine pair copula families Θ and their parameters Σ may be modeled as latent variables to enable flexibility in the selection of the D-vine pair copula families and their parameters, based on the dependency within the data, on the basis of an a priori Bayesian model. The generative model of the D-vine copula may in itself entail sampling a plurality of latent variables associated with the D-vine based on the rank-transformed historical data. For adaptive non-parametric Bayesian clustering using the extended generative model, the number of mixture components associated with the data of each data view may be chosen by placing a DP prior to a mixture distribution. In an embodiment, a vector of mixture weights π may be drawn using the stick-breaking process with a concentration parameter α that may, in turn, be modeled as a random variable with a gamma prior. The extended generative process may further include a selection of a mixture component $Z = \{Z_i\}$ for each observation i, based on the mixture distribution. That is, the latent variable Z may be generated for use in the distribution of data of the one or more medical records into each of the one or more clusters. Further, the marginal latent variable $U = \{U_{i,v,j}\}$ may be generated from a D-vine with uniform marginals. Thereafter, an inverse cumulative distribution of the marginal latent variable U may be computed to obtain the observed data $X = \{X_{i,v,j}\}$ in a manner similar to the generative model of a D-vine (as in equations (7a) and (7b)). The entire extended generative model using the DP for multi-view clustering is summarized in equations (8a) to (8g) below:

$$\alpha \sim Gamma(a,b) \quad (8a)$$

$$\pi \sim GEM(\alpha) \quad (8b)$$

$$\forall k,v,s,t; \theta_{k,v,s,t} \sim Unif(1:T) \quad (8c)$$

$$\forall k,v,s,t; \sigma_{k,v,s,t}|\theta_{k,v,s,t} \sim Prior(\sigma_{k,v,s,t}) \quad (8d)$$

$$\forall i \in 1,\ldots,N; Z_i|\pi \sim \pi \quad (8e)$$

$$\forall i,v; U_{i,v}|Z_i,k,\theta,\Sigma \sim DVine(\Theta_{k,v}, \Sigma_{k,v}) \quad (8f)$$

$$\forall i,v,j; X_{i,v,j} = F_{v,j}^{-1}(U_{i,v,j}) \quad (8g)$$

where,

α: a random variable that corresponds to a concentration parameter of DP;

Gamma (a,b): gamma prior function;

π: a vector of mixture weights;

GEM ( ): a stick-breaking distribution over π;

Unif ( ): uniform distribution;

$\theta_{k,v,s,t}, \sigma_{k,v,s,t}$: parameters for pair copula $C_{s,t/s+1,\ldots s+t-1}$;

DVine ($\Theta_{k,v}, \Sigma_{k,v}$): D-vine pair copula families $\Theta_{k,v}$ with parameters $\Sigma_{k,v}$ for cluster k and data view v; and Prior ( ): a priori Bayesian distribution.

The aforementioned extended generative model of D-vine pair copula families associated with a D-vine mixture model during DP, as per equations (8a) to (8g), require inference of random variables, such as U, Σ, θ, Z, and α. These random variables are also hereinafter referred to as latent variables. There may be two challenges in the inference of the aforementioned latent variables, the first being presence of data with both discrete and continuous marginals and the second being non-conjugacy of priors for various latent variables. As discussed in step 304, by the application of the rank transformation on the historical data, inference of marginals may no longer be required and further mixed data within the historical data may be handled, thereby overcoming the first challenge. In addition, use of a Gibbs sampling approach that incorporates use of a Bayesian non-parametric modeling technique may handle the second issue of non-conjugate latent variable priors. In an embodiment, though the random variable π may also be needed to be inferred along with the rest of the latent variables, the random variable π may be integrated out due to conjugacy. Further, the sampling of the random latent variable α may be performed using one or more techniques known in the art (e.g., Bayesian estimation). The sampling of the remaining one or more latent variables, such as Z, U, Σ, and θ and consequent estimation of these one or more latent variables is explained next in step 310.

At step 310, one or more latent variables from the plurality of latent variables may be estimated based on a first value, a second value, and a third value. In an embodiment, the processor 202 may be configured to estimate the one or more latent variables from the plurality of latent variables based on the first value, the second value, and the third value. The first value, denoted by $n_k$, may indicate a count of the one or more records clustered in a cluster k from the one or more clusters corresponding to a data view v. The second value, denoted by N, may indicate a count of the one or more medical records in the historical data. The third value, denoted by α, may correspond to a parameter that may be utilized to predict a fourth value. The fourth value may correspond to a probability of the selection of a D-vine pair copula family from the one or more D-vine pair copula families to model a cluster from the one or more clusters corresponding to a data view. That is, the third value a (the concentration parameter of a DP) may be used to categorize data of each data view within the historical data into different mixture components or clusters by providing a probability of assigning a mixture component or cluster to the data. The D-vine pair copula family may be selected from the one or more D-vine pair copula families based on this probability of assignment of mixture component or cluster to data of a data view within the historical data. For instance, the dependency structure of data within a certain data view can be modeled using a particular family of D-vine pair copula. The specific D-vine pair copula family may be selected from one or more D-vine pair copula families associated with a D-vine mixture model, based on a probability of assigning the data in data view to a category modeled by that D-vine pair copula family. The estimation of the latent variables U, Z, Σ, and θ by sampling of the latent variables U, Z, Σ, and Θ may be based on the first value (i.e., $n_k$), the second value (i.e., N), and the third value (i.e., α), as explained next in conjunction with Algorithms 1 and 2.

Algorithm 1: Gibbs Sampling Inference Scheme for Rank Likelihood Based Estimation of Mixture of D-Vines:

1. for each i = 1, . . . N do
2. $p(Z_i = k \mid Z_{-i}, U, \sum, \Theta, D_i, \ldots) \propto \frac{n_k}{N+\alpha} p(U_i, \ldots \mid Z_i = k, \sum, \Theta) \delta(k \in C_i)$ //where, $C_i$ is given by equation 10
3. for each i = 1, . . . N do
4. for each v = 1, . . . V do
5. for each j = 1, . . . $M_v$ do
6. $U_{i,v,\cdot} \sim DVine(\Theta_{k,v}, \Sigma_{k,v}) \mid U_{i,v,\cdot} \in D_{i,v,\cdot} \forall j$
//where, sampling of $U_{i,v,j}$ is as per algorithm 2
7. for each k = 1, . . . K do
8. for each v = 1, . . . V do
9. for each t = 1, . . . $M_v$ − 1 do
10. for each s = 1, . . . $M_v$ − t do
11. $\sigma_{k,v,s,t}, \theta_{k,v,s,t} \sim p(\sigma_{k,v,s,t}, \theta_{k,v,s,t} \mid W_{k,v,s,t})$
// where, sampling of Dvine parameters is as per equation 12 (Metropolis Hastings)
12. Sample Hyper parameter $\alpha \sim p(\alpha \mid K, N)$ using DP based Monte Carlo technique Algorithm 2: Sampling from D-Vine with Rank Constraints within Each Cluster:

1. for each j=1,...,$M_v$ do
2. $U_{i,v,j}^{k,Low} = \max\{U_{r,v,j}: Z_r = k, X_{r,v,j} < X_{i,v,j}\}$
3. $U_{i,v,j}^{k,High} = \min\{U_{r,v,j}: Z_r = k, X_{r,v,j} > X_{i,v,j}\}$
4. if j==1 then
5. $U_{i,v,1} \sim Unif(U_{i,v,j}^{k,Low}, U_{i,v,j}^{k,High})$
6. else
7. $R^{Low} = F(U_{i,v,j}^{k,Low} \mid U_{i,v,1}, \ldots, U_{i,v,j-1})$
8. $R^{High} = F(U_{i,v,j}^{k,High} \mid U_{i,v,1}, \ldots, U_{i,v,j-1})$
9. $R \sim Unif(R^{Low}, R^{High})$
10. for l in 2:j-1 do
11. $R = h^{-1}(R, F(U_{i,v,j-1} \mid U_{i,v,1}, \ldots, U_{i,v,j-1}))$
12. $U_{i,v,j} = h^{-1}(R, U_{i,v,j-1})$ Sampling of the latent variable U: For each data view, the latent variable representing the marginal distribution $U_{i,v}$ that belongs to a cluster k may be updated based on sampling from an appropriate D-vine pair copula family with parameters $\Theta_{k,v}$ and $\Sigma_{k,v}$, which models the cluster k and data view v. The latent variable $U_{i,v}$ may be independent across the multiple data views V (e.g., the multi-view dataset 112) to capture data dependency across the data views, while each D-vine pair copula family may capture intra-data view data dependency. The update of the latent variable $U_{i,v}$ is shown in lines 3 to 6 of the Algorithm 1. The sampling from the D-vine may be as per the Algorithm 2, which may be based on additional rank constraints of the extended rank likelihood technique. Thus, each $U_{i,v}$, ∀i, v may be constrained such that elements of the set $U^k = \{U_i, \ldots : i \in [N], Z_i = k\}$ may follow the original rank order of the observations in the cluster for each dimension and data view after the update.

The lower and upper bounds for each dimension j for each data view v for the latent variable $U_{i,v,j}$ may be ascertained based on other members of the same cluster k, given as $Z_i = k$, as shown in lines 2 and 3 of the Algorithm 2. For each data view v, each observation i with $Z_i = k$ as given, the constraint set for the extended rank likelihood technique may be defined, as represented by equation (9), as follows:

$$D_{i,v,j} = \{u \in [0,1]: U_{i,v,j}^{k,Low} < u < U_{i,v,j}^{k,High}\} \quad (9)$$

Based on sampling from a D-vine that may be constrained to lie within the set $D_{i,v,j}$ defined in equation (9), the latent variable $U_{i,v}$ may be updated for each dimension j, as shown in line 6 of Algorithm 1. The process of sampling from the D-vine with rank constraints, as per Algorithm 2, is explained next.

Sampling from a D-vine with rank constraints (as per Algorithm 2): The latent variable $U_{i,v}$ may be sampled by sampling $U_{i,v,1}$ from $p(U_{i,v,1} \mid \Sigma; U_{i,v,1} \in D_{i,v,1})$, $U_{i,v,2}$ from $p(U_{i,v,2} \mid \Sigma, U_{i,v,1}; U_{i,v,2} \in D_{i,v,2})$, and so on until the sampling of $U_{i,v,M_v}$ from $p(U_{i,v,M_v} \mid \Sigma, U_{i,v,1}, \ldots, U_{i,v,M_v-1}; D_{i,v,M_v} \in D_{i,v,M_v})$. In an embodiment, the cumulative distribution for the conditions of $U_{i,v,j}$ may have a closed form and may be expressed in the form of an invertible h-function (an example of an h-function is illustrated in equation (6)). Therefore, an inverse transform sampling of the corresponding h-function of the cumulative distribution of the conditions, bound by the rank constraint $D_{i,v,j}$, may be used to obtain the update of the sampled value of the latent variable $U_{i,v,j}$.

Sampling of the latent variable Z: The latent variable Z may be used for cluster assignment across the data within the various data views associated with the historical data. In an embodiment, the latent variable Z may be sampled based on a predictive distribution (e.g., a Gamma distribution) that may be generated based on a Dirichlet Process (DP). The probability of $Z_i$ being assigned a value k may be based on the product of two terms. The first term $p(Z_i = k \mid Z_{-i})$ may be based on the distribution generated by the DP process (where "−i" corresponds to records excluding the $i^{th}$ record in the historical data), while the second term $p(U_i, \ldots \mid Z_i = k,$ $\Sigma$, $\Theta$) may be based on the extended rank likelihood technique. However, $Z_i$ may be constrained based on a set $C_i$ of permissible clusters that satisfy the rank constraints. That is, $\forall k \in [K]$, $Z_i = k$ may be a permissible cluster if $U^k \cup U_i, \ldots$ satisfies the rank constraints. The set of permissible clusters Ci may be defined, as represented by equation (10), as follows:

$$C_i = \{k: \{U_{i,\ldots}^{k,Low}\} < U_i, \ldots < \{U_{i,v,j}^{k,High}\}\} \quad (10)$$

The update for the sampling of the latent variable $Z_i$ is shown in line 2 of Algorithm 1. In an embodiment, to compute the probability of $Z_i = k_{new}$ (that is, probability to assign a fresh cluster or mixture component, $p(Z_i = k_{new})$), the prior distributions of the parameters $\Sigma_{k_{new},v}$ of the new cluster and the corresponding D-vine pair copula families $\Theta_{k_{new},v}$ may be integrated. A Markov Chain Monte Carlo (MCMC)-based estimation technique may be used to perform the integral of the prior distributions of the parameters to obtain the probability of the new cluster $k_{new}$, and in turn sample the latent variable $Z_i$. Further, the hyper parameter $\alpha$ may also be sampled using the MCMC technique.

Sampling of the parameters $\Sigma$ and $\Theta$ of the D-vine pair copula families: In an embodiment, Metropolis-Hastings technique may be used in the Gibbs sampling update for the latent variable parameters $\Sigma$ and $\Theta$, as the priors of these latent variable parameters may be non-conjugate. Accordingly, a uniform prior may be placed on $\theta_{k,v,s,t}$; $\forall s<t$, $\forall k, v$ to select a D-vine pair copula family with a probability of "1/T" from one of "T" preselected D-vine pair copula families. Similarly, a uniform prior may be placed on $\sigma_{k,v,s,t}$; $\forall s<t$, $\forall k, v$ for each D-vine pair copula family in the D-vine mixture model. However, in case of a bivariate Gaussian copula family, the priors of the latent variable parameters $\Sigma$ and $\Theta$ may be conjugate. In such a scenario, an inverse Wishart prior may be used to sample these latent variable parameters to exploit the conjugacy of these latent variables. In an embodiment, the D-vine pair copula families $\Theta_{k,v}$ and the parameters $\Sigma_{k,v}$ for the D-vine pair copula corresponding to each cluster k and each data view v may be jointly sampled and conditioned based on the latent variables generated in the extended generative model.

As per the D-vine mixture model, parameters of the D-vine pair copulas at the first level may be based on a pair of dimensions in the rank-transformed historical data, sampled in the form of respective marginal distributions of the latent variable U. The parameters of the D-vine pair copulas at higher levels in the D-vine mixture model hierarchy may be based on conditionals of the preceding level D-vine pair copula distributions. Thus, for the first level, Gibbs sampling update for the D-vine pair copula parameters $\Sigma_{k,v,s,t}$ may be conditioned on the set of pairs defined as $W_{k,v,s,t} = \{U_{i,v,s}, U_{i,v,t}: Z_i = k\}$. Further, the set of pairs that may condition the D-vine pair copula parameters $\Sigma_{k,v,s,t}$ at higher levels (when $t > s+1$) may be defined, as represented by equation (11), as follows:

$$W_{k,v,s,t} = \{F(U_{i,v,s}|U_{i,v,s+1}, \ldots U_{i,v,s+t-1}), F(U_{i,v,t}|U_{i,v,s+1}, \ldots U_{i,v,s+t-1}): Z_i = k\} \quad (11)$$

In an embodiment, the D-vine pair copula family parameters $\sigma_{k,v,s,t}$ and $\theta_{k,v,s,t}$ may be sampled using the conditional probability, based on the Metropolis-Hastings technique, as represented by equation (12), as follows:

$$(\sigma_{k,v,s,t}, \theta_{k,v,s,t}|W_{k,v,s,t}) \propto p(\theta_{k,v,s,t}) p(\sigma_{k,v,s,t}) p(W_{k,v,s,t}|\sigma_{k,v,s,t}, \theta_{k,v,s,t}) \quad (12)$$

The sampling of the D-vine pair copula family parameters $\sigma_{k,v,s,t}$ and $\theta_{k,v,s,t}$ is also shown in line 11 of the Algorithm 1. Based on the sampling of the parameters $\sigma_{k,v,s,t}$ and $\theta_{k,v,s,t}$, the Gibbs sampling update for the families defined by latent variable parameter $\Theta$ and each D-vine pair copula defined by parameter $\Sigma$ in the D-vine mixture model may be obtained. Thus, the latent variable parameters $\Sigma$ and $\Theta$ may be sampled.

A person skilled in the art will understand that the scope of the disclosure should not be limited to use of a Gibbs sampling technique to sample the plurality of latent variables. Various other statistical techniques known in the art, such as but not limited to, Bayesian technique, Monte Carlo technique, and expectation maximization (EM) technique, may be used to sample the plurality of latent variables without departure from the spirit of the disclosure.

At step 312, the D-vine mixture model may be generated based on the estimated one or more latent variables from the plurality of latent variables. In an embodiment, the processor 202 may be configured to generate the D-vine mixture model. In an embodiment, the D-vine mixture model may include a selected D-vine pair copula family for each cluster associated with each of the multi-view dataset 112.

At step 314, a classifier may be trained based on the generated D-vine mixture model. In an embodiment, the processor 202 may be configured to train the classifier. In an embodiment, the processor 202 may determine each D-vine pair copula associated with the D-vine mixture model based on the respective one or more parameters of the bivariate copula distributions, as discussed above. In an embodiment, the one or more D-vine pair copula associated with the D-vine mixture model may be deterministic of the one or more health conditions of the one or more first human subjects in the historical data. In an embodiment, the processor 202 may train the classifier based on the one or more D-vine pair copula associated with the D-vine mixture model and the historical data, using one or more machine-learning techniques known in the art. Examples of the classifier may include, but are not limited to, an SVM, a logistic regression, a Bayesian classifier, a decision tree classifier, a copula-based classifier, a KNN classifier, or an RF classifier. A person skilled in the art will appreciate that the scope of the disclosure is not limited to the training of the classifier, as discussed above. The classifier may be trained using any machine learning or artificial intelligence technique known in the art without departing from the spirit of the disclosure.

Figure 4:
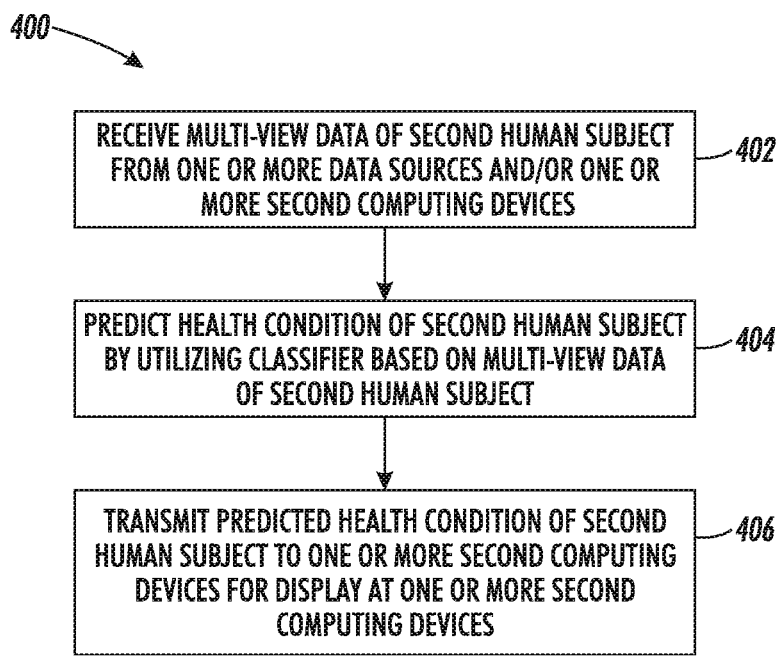
FIG. 4 illustrates a flowchart of a method for predict a health condition of a human subject, in accordance with at least one embodiment.

FIG. 4 illustrates a flowchart of a method to predict the health condition of a human subject, in accordance with at least one embodiment. With reference to FIG. 4, a flowchart 400 is shown and described in conjunction with FIGS. 1-3.

At step 402, multi-view data of a second human subject may be received. In an embodiment, the processor 202 may be configured to receive the multi-view data of the second human subject, via the transceiver 206, through the communication network 114. The multi-view data of the second human subject may be received from one or more data sources (e.g., DS_1 112a and DS_2 112b). The multi-view data may also be received from one or more second computing devices (e.g., the human-subject computing device 106 of the second human subject and/or a computing device of a medical practitioner associated with the second human subject). In an embodiment, the multi-view data may at least include data associated with a physiological-parameters data view, which may include a measure of one or more physiological parameters of the second human subject. The multi-view data may also include other details of the second human subject, including data associated with a demographic-details data view, a social-behavior data view, and/or a past addictions data view. In an embodiment, the processor 202 may receive the measure of the one or more physiological parameters and/or the other details of the second human subject from the human-subject computing device 106 of the second human subject in real-time or otherwise (e.g., periodically or asynchronously). In an embodiment, as discussed, the set of biosensors 108 may be inbuilt within the human-subject computing device 106. Alternatively, the set of biosensors 108 may be communicatively coupled to the human-subject computing device 106 through the set of DAQ interfaces 110. In an embodiment, the set of biosensors 108 may measure the one or more physiological parameters of the second human subject in real-time. Thereafter, the human-subject computing device 106 may send the one or more physiological parameters and/or the other details of the second human subject to the processor 202 either in real time or otherwise (e.g., periodically or asynchronously).

At step 404, a health condition of the second human subject may be predicted using the trained classifier. In an embodiment, the processor 202 may be configured to predict the health condition of the second human subject using the trained classifier based on the multi-view data of the second human subject. Further, the processor 202 may display the predicted health condition of the second human subject through a user-interface on the human-subject computing device 106 of the second human subject. In an embodiment, the health condition may correspond to at least one of a mortality risk, a disease risk, a disease symptom, an onset of a disease, a recovery from a disease, or an effect of medications for a disease.

At step 406, the predicted health condition of the second human subject is transmitted to one or more second computing devices. In an embodiment, the processor 202 may be configured to transmit information pertaining to the predicted health condition of the second human subject to the one or more second computing devices, via the transceiver 206, over the communication network 114. In an embodiment, the one or more second computing devices may correspond to one or more of: the human-subject computing device 106 of the second human subject, or a computing device of a medical practitioner associated with the second human subject. In an embodiment, the one or more second computing devices may also include a computing device at a healthcare facility associated with the treatment of the second human subject or a computing device of a caregiver associated with the second human subject. Once the predicted health condition transmitted by the processor 202 is received by the one or more second computing devices, the information pertaining to the predicted health condition of the second human subject may be displayed on a display of the one or more second computing devices. For instance, the predicted health condition of the second human subject may be displayed to the second human subject on a display screen of the human-subject computing device 106 of the second human subject.

A person having ordinary skill in the art will understand that the scope of the disclosure should not be limited to determining a health condition of a human subject. In an embodiment, similar medical data may be analyzed to make various inferences. For instance, insurance data pertaining to healthcare may be analyzed to determine health insurance frauds.

Further, the disclosure may be implemented to analyze data from various levels of the healthcare industry, such as at the individual patient level through analysis of electronic medical records (EMR), or at hospital level (e.g., identifying a group of patients having the risk of getting involved in health insurance frauds). For example, the historical data may correspond to a multivariate dataset, including medical insurance records of one or more individuals. In such a scenario, an M-dimensional variable in each medical insurance record may correspond to one or more insurance-related parameters, such as age of an insured person, one or more physiological parameters of the insured person, premium being paid by the insured person, insurance amount, coverage limit, and so on. Thus, the process described in the flowchart 300 may be utilized to determine insurance frauds, recommend insurance amounts, and/or the like.

Further, a person skilled in the art will appreciate that the scope of the disclosure should not be limited to predicting the health condition of the first human subject. In an embodiment, the disclosure may be implemented for identifying one or more categories in any multivariate dataset. Further, the disclosure may be implemented for predicting a category from the one or more categories into which a new record of the multivariate dataset may be classified. For example, the disclosure may be implemented to analyze a financial dataset to determine a credit risk category of a customer. Further, the financial dataset may be analyzed to categorize the customers in one or more categories of buying behaviors. The financial dataset may include various types of financial data such as, but not limited to, loan risk assessment data, insurance data, bank statements, and bank transaction data.

The disclosed embodiments encompass numerous advantages. The disclosure leads to an effective clustering of a multivariate dataset using a D-vine copula mixture model with the flexibility to choose a best-fit D-vine pair copula family to model each cluster. In scenarios where the data set includes data from multiple data views or data sources, it may be beneficial to simultaneously model data dependency within each data view and data dependency across the various data views. However, simultaneous modeling of such an intra- and inter-data view data dependency may be a non-trivial task. According to the disclosure, an appropriate D-vine pair copula family associated with a D-vine mixture model may be selected from a set of D-vine pair copula families to model each of one or more clusters assigned to the data of each data view. The dependency structure of data within the data view may be modeled by the D-vine pair copula families modeling the various clusters that may be assigned to data of that data view. Further, the D-vine mixture model (generated from the sampling update of the latent variable U), as a whole, including a collection of such D-vine pair copula families selected for each cluster, may be used to model the dependency structure of the data within and across the data views in real time.

The disclosed method and system, as illustrated in the ongoing description or any of its components, may be embodied in the form of a computer system. Typical examples of a computer system include a general-purpose computer, a programmed microprocessor, a micro-controller, a peripheral integrated circuit element, and other devices or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The system and method described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++," and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating system and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above method and system, or the numerous possible variations thereof.

Various embodiments of method and system for data processing to predict health condition of a human subject have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different system or applications.

Those skilled in the art will appreciate that any of the aforementioned steps and/or system modules may be suitably replaced, reordered, or removed, and additional steps and/or system modules may be inserted, depending on the needs of a particular application. In addition, the system of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different system or applications. Presently unforeseen or unanticipated alternatives, modifications, variations, or improvements therein may be subsequently made by those skilled in the art, which are also intended to be encompassed by the following claims.

What is claimed is:

1. A method for delivering a health condition profile to a human subject computing device for recommending a course of treatment, the method comprising:

receiving, by one or more transceivers in an application server, historical data comprising one or more records of one or more first human subjects from a database server over a communication network, wherein each of the one or more records includes data corresponding to a plurality of data views comprising a physiological-parameter data view comprising a measure of each of one or more physiological parameters of the one or more first human subjects including at least one of: age, cholesterol level, heart rate, blood pressure, breath carbon-dioxide concentration, breath oxygen concentration, stroke score, blood creatinine level, blood albumin level, blood sodium level, total blood count, blood glucose/sugar level, blood hemoglobin level, and blood platelet count;

for each of the plurality of data views:

clustering, by one or more processors in the application server, data corresponding to the data view in the historical data into one or more clusters, wherein each of the one or more clusters is modeled using a D-vine pair copula family from one or more D-vine pair copula families associated with a D-vine mixture model, by sampling a plurality of latent variables based on a rank transformation of the historical data;

estimating, by the one or more processors, one or more latent variables from the plurality of latent variables based on at least:

a first value indicative of a count of the one or more records clustered in a cluster from the one or more clusters corresponding to the data view, a second value indicative of a count of the one or more records, and a third value indicative of a parameter utilizable to determine a fourth value, wherein the fourth value corresponds to a probability of selecting the D-vine pair copula family from the one or more D-vine pair copula families to model the cluster from the one or more clusters corresponding to the data view;

generating, by the one or more processors, the D-vine mixture model including the selected D-vine pair copula family for each of the plurality of data views, based on the estimated one or more latent variables from the plurality of latent variables;

training, by the one or more processors, a classifier based on the generated D-vine mixture model, the classifier configured to sort data into one or more health condition categories, each health condition category corresponding to a health condition, wherein the health condition corresponds to at least one of a mortality risk, a disease risk, a disease symptom, an onset of a disease, a recovery from a disease, or an effect of medications for a disease;

measuring, by a biosensor associated with the human subject computing device, one or more physiological parameters of a second human subject including at least one of: age, cholesterol level, heart rate, blood pressure, breath carbon-dioxide concentration, breath oxygen concentration, stroke score, blood creatinine level, blood albumin level, blood sodium level, total blood count, blood glucose/sugar level, blood hemoglobin level, and blood platelet count;

receiving, by the one or more transceivers, multi-view data comprising the one or more physiological parameters of the second human subject from the human subject computing device over the communication network;

sorting, by the one or more processors, utilizing the trained classifier the received multi-view data into one or more of the health condition categories;

assigning, by the one or more processors, a health condition profile to the second human subject, the health condition profile comprising one or more health conditions corresponding to the one or more categories into which the multi-view data is sorted;

delivering, by the one or more transceivers, the health condition profile of the second human subject to the human subject computing device over the communication network; and displaying the health condition profile of the second human subject on the a display device of the human subject computing device for recommending the course of treatment for the second human subject.

2. The method of claim 1, wherein the one or more latent variables include one or more parameters associated with the selected D-vine pair copula family for each of the plurality of data views, a marginal distribution of each dimension associated with a data view from the plurality of data views, and/or a distribution of the one or more records into each of the one or more clusters.

3. The method of claim 2, wherein the one or more parameters are estimated by utilizing one of a Gibbs sampling technique, an Expectation-Maximization (EM) technique, or a Markov Chain Monte Carlo (MCMC) technique.

4. The method of claim 2, wherein the one or more parameters are estimated based on one of an inverse Wishart distribution, a Metropolis-Hastings technique, and/or a Dirichlet Process technique.

5. The method of claim 2, wherein the one or more parameters comprise at least a covariance matrix associated with a D-vine pair copula family.

6. The method of claim 1, wherein a D-vine pair copula family models a dependency between a pair of dimensions from one or more dimensions in each of the one or more records, wherein a first set of dimensions from the one or more dimensions include continuous data and a second set of dimensions from the one or more dimensions include discrete data.

7. The method of claim 1, wherein the rank transformation corresponds to an extended rank likelihood technique.

8. The method of claim 1, wherein a data type associated with the historical data corresponds to at least one of a numerical data type or a categorical data type.

9. The method of claim 1, wherein the historical data corresponds to a multivariate dataset from which the health condition is identifiable based on the generated D-vine mixture model.

10. The method of claim 1, wherein the measuring of each of the one or more physiological parameters of the second human subject occurs in real-time.

11. A health condition profile delivery system for recommending a course of treatment, the system comprising:
    an application server comprising one or more transceivers and one or more processors;
    a communication network;
    a database server;
    a biosensor; and
    a human subject computing device comprising a display device associated with the biosensor;
    the one or more transceivers in the application server configured to:
    receive historical data comprising one or more records of one or more first human subjects from the database server over the communication network, wherein each of the one or more records includes data corresponding to a plurality of data views comprising a physiological-parameter data view comprising a measure of each of one or more physiological parameters of the one or more first human subjects including at least one of: age, cholesterol level, heart rate, blood pressure, breath carbon-dioxide concentration, breath oxygen concentration, stroke score, blood creatinine level, blood albumin level, blood sodium level, total blood count, blood glucose/sugar level, blood hemoglobin level, and blood platelet count; and
    for each of the plurality of data views, the one or more processors in the application server configured to:
    cluster data corresponding to the data view in the historical data into one or more clusters, wherein each of the one or more clusters is modeled using a D-vine pair copula family from one or more D-vine pair copula families associated with a D-vine mixture model, by sampling a plurality of latent variables based on a rank transformation of the historical data;
    estimate one or more latent variables from the plurality of latent variables based on at least:
        a first value indicative of a count of the one or more records clustered in a cluster from the one or more clusters corresponding to the data view,
        a second value indicative of a count of the one or more records, and
        a third value indicative of a parameter utilizable to determine a fourth value, wherein the fourth value corresponds to a probability of selecting the D-vine pair copula family from the one or more D-vine pair copula families to model the cluster from the one or more clusters corresponding to the data view;

generate the D-vine mixture model including the selected D-vine pair copula family for each of the plurality of data views, based on the estimated one or more latent variables from the plurality of latent variables; and train a classifier based on the generated D-vine mixture model, the classifier configured to sort data into one or more health condition categories, each health condition category corresponding to a health condition, wherein the health condition corresponds to at least one of a mortality risk, a disease risk, a disease symptom, an onset of a disease, a recovery from a disease, or an effect of medications for a disease, wherein the biosensor is configured to measure one or more physiological parameters of a second human subject including at least one of: age, cholesterol level, heart rate, blood pressure, breath carbon-dioxide concentration, breath oxygen concentration, stroke score, blood creatinine level, blood albumin level, blood sodium level, total blood count, blood glucose/sugar level, blood hemoglobin level, and blood platelet count;

the one or more transceivers are further configured to receive multi-view data comprising the one or more physiological parameters of the second human subject from the human subject computing device over the communication network, the one or more processors are further configured to sort, utilizing the trained classifier, the received multi-view data into one or more of the health condition categories, the one or more processors are further configured to assign a health condition profile to the second human subject, the health condition profile comprising one or more health conditions corresponding to the one or more categories into which the multi-view data is sorted, the one or more transceivers are further configured to deliver the health condition profile of the second human subject to the human subject computing device over the communication network; and the display device is configured to display the health condition profile of the second human subject for recommending the course of treatment for the second human subject.

12. The system of claim 11, wherein the one or more latent variables include one or more parameters associated with the selected D-vine pair copula family for each of the plurality of data views, a marginal distribution of each dimension associated with a data view from the plurality of data views, and/or a distribution of the one or more records into each of the one or more clusters.

13. The system of claim 12, wherein the one or more parameters are estimated by utilizing one of a Gibbs sampling technique, an Expectation-Maximization (EM) technique, or a Markov Chain Monte Carlo (MCMC) technique.

14. The system of claim 12, wherein the one or more parameters are estimated based on one of an inverse Wishart distribution, a Metropolis-Hastings technique, and/or a Dirichlet Process technique.

15. The system of claim 12, wherein the one or more parameters comprise at least a covariance matrix associated with a D-vine pair copula family.

16. The system of claim 11, wherein a D-vine pair copula family models a dependency between a pair of dimensions from one or more dimensions in each of the one or more records, wherein a first set of dimensions from the one or more dimensions include continuous data and a second set of dimensions from the one or more dimensions include discrete data.

17. The system of claim 11, wherein the rank transformation corresponds to an extended rank likelihood technique.

18. The system of claim 11, wherein a data type associated with the historical data corresponds to at least one of a numerical data type or a categorical data type.

19. The system of claim 11, wherein the historical data corresponds to a multivariate dataset from which the health condition is identifiable based on the generated D-vine mixture model.

20. The system of claim 11, wherein the measure of each of the one or more physiological parameters of the second human subject occurs in real-time.

21. A computer program product for use with a an application server in delivery of a health condition profile to a human subject computing device for recommending a course of treatment, wherein the computer program code is executable by one or more processors in the first computing device to:

receive, by the one or more transceivers in the application server, historical data comprising one or more records of one or more first human subjects from a database server over a communication network, wherein each of the one or more records includes data corresponding to a plurality of data views comprising a physiological-parameter data view comprising a measure of each of one or more physiological parameters of the one or more first human subjects including at least one of: age, cholesterol level, heart rate, blood pressure, breath carbon-dioxide concentration, breath oxygen concentration, stroke score, blood creatinine level, blood albumin level, blood sodium level, total blood count, blood glucose/sugar level, blood hemoglobin level, and blood platelet count; for each of the plurality of data views:

cluster, by one or more processors in the application server, data corresponding to the data view in the historical data into one or more clusters, wherein each of the one or more clusters is modeled using a D-vine pair copula family from one or more D-vine pair copula families associated with a D-vine mixture model, by sampling a plurality of latent variables based on a rank transformation of the historical data;

estimate, by the one or more processors, one or more latent variables from the plurality of latent variables based on at least:

a first value indicative of a count of the one or more records clustered in a cluster from the one or more clusters corresponding to the data view, a second value indicative of a count of the one or more records, and a third value indicative of a parameter utilizable to predict a fourth value, wherein the fourth value corresponds to a probability of selecting the D-vine pair copula family from the one or more D-vine pair copula families to model the cluster from the one or more clusters corresponding to the data view;

generate, by the one or more processors, the D-vine mixture model including the selected D-vine pair copula family for each of the plurality of data views, based on the estimated one or more latent variables from the plurality of latent variables;

train, by the one or more processors, a classifier based on the generated D-vine mixture model, the classifier configured to sort data into one or more health condition categories, each health condition category corresponding to a health condition, wherein the health condition corresponds to at least one of a mortality risk, a disease risk, a disease symptom, an onset of a disease, a recovery from a disease, or an effect of medications for a disease;

receive, by the one or more transceivers, multi-view data comprising one or more physiological parameters of a second human subject from the human subject computing device over the communication network, the one or more physiological parameters measured by a biosensor associated with the human subject computing device, the one or more physiological parameters including at least one of: age, cholesterol level, heart rate, blood pressure, breath carbon-dioxide concentration, breath oxygen concentration, stroke score, blood creatinine level, blood albumin level, blood sodium level, total blood count, blood glucose/sugar level, blood hemoglobin level, and blood platelet count;

sort, by the one or more processors, utilizing the trained classifier, the received multi-view data into one or more of the health condition categories;

assign, by the one or more processors, a health condition profile to the second human subject, the health condition profile comprising one or more health conditions corresponding to the one or more categories into which the multi-view data is sorted; and deliver, by the one or more transceivers, the health condition profile of the second human subject to the human subject computing device over the communication network, wherein the health condition profile of the second human subject is displayed on a display device of the human subject computing device for recommending the course of treatment for the second human subject.

* * * * *